United States Patent
Radicke

(10) Patent No.: US 9,402,594 B2
(45) Date of Patent: Aug. 2, 2016

(54) X-RAY DETECTOR OF A GRATING-BASED PHASE CONTRAST X-RAY DEVICE AND METHOD FOR OPERATING A GRATING-BASED PHASE CONTRAST X-RAY DEVICE

(75) Inventor: Marcus Radicke, Fuerth (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 100 days.

(21) Appl. No.: 14/345,287

(22) PCT Filed: Sep. 3, 2012

(86) PCT No.: PCT/EP2012/067108
§ 371 (c)(1),
(2), (4) Date: Mar. 17, 2014

(87) PCT Pub. No.: WO2013/037656
PCT Pub. Date: Mar. 21, 2013

(65) Prior Publication Data
US 2014/0341347 A1    Nov. 20, 2014

(30) Foreign Application Priority Data

Sep. 16, 2011    (DE) .................. 10 2011 082 878

(51) Int. Cl.
*A61B 6/00*    (2006.01)
*G01N 23/04*   (2006.01)
*G01N 23/20*   (2006.01)

(52) U.S. Cl.
CPC ............... *A61B 6/484* (2013.01); *A61B 6/4233* (2013.01); *A61B 6/4266* (2013.01);
(Continued)

(58) Field of Classification Search
CPC .. A61B 6/4233; A61B 6/4266; A61B 6/4291; A61B 6/484; A61B 6/5205
USPC ................... 378/19, 36, 98.8, 62; 250/370.09
See application file for complete search history.

(56) References Cited

U.S. PATENT DOCUMENTS

| 5,812,629 A | 9/1998 | Clauser |
| 6,069,933 A | 5/2000 | Schultz |

(Continued)

FOREIGN PATENT DOCUMENTS

| CN | 1748645 A | 3/2006 |
| CN | 101011251 A | 8/2007 |

(Continued)

OTHER PUBLICATIONS

Harold H. Wen, Eric E. Bennett, Rael Kopace, Ashley F. Stein and Vinay Pai Single-shot x-ray differential phase-contrast and diffraction imaging using two-dimensional transmission gratings Optics Letters, vol. 35 No. 12 pp. 1932-1934; 2010; US; Jun. 15, 2010.

(Continued)

*Primary Examiner* — Allen C. Ho
(74) *Attorney, Agent, or Firm* — Laurence Greenberg; Werner Stemer; Ralph Locher

(57) ABSTRACT

An x-ray detector of a grid-based phase-contrast x-ray device and a method for operating a grid-based phase-contrast x-ray device. Signal values of detector elements are combined to form group signal values. An image computing unit calculates an x-ray beam phase value from the group signal values.

33 Claims, 14 Drawing Sheets

Figure 1:
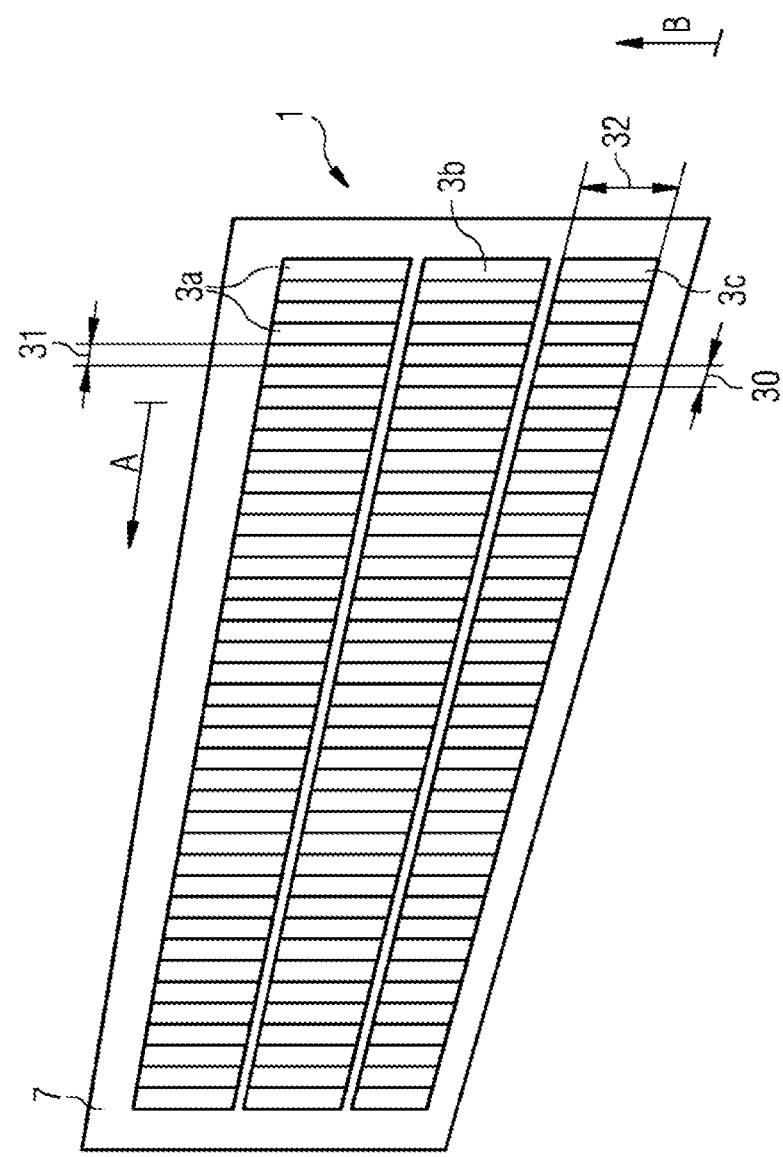

(52) U.S. Cl.
CPC ............ *A61B 6/4291* (2013.01); *A61B 6/5205* (2013.01); *G01N 23/04* (2013.01); *G01N 23/20075* (2013.01); *G01N 2223/501* (2013.01); *G01N 2223/6123* (2013.01)

(56) References Cited

U.S. PATENT DOCUMENTS

| | | | |
|---|---|---|---|
| 6,389,096 B1 * | 5/2002 | Hoffman | A61B 6/032 378/19 |
| 6,826,255 B2 | 11/2004 | Birdwell et al. | |
| 6,834,994 B2 | 12/2004 | Ozawa et al. | |
| 7,433,444 B2 * | 10/2008 | Baumann | A61B 6/032 378/145 |
| 7,492,871 B2 * | 2/2009 | Popescu | A61B 6/00 378/145 |
| 7,522,698 B2 * | 4/2009 | Popescu | A61B 6/032 378/19 |
| 7,522,708 B2 * | 4/2009 | Heismann | A61B 6/00 378/145 |
| 7,532,704 B2 * | 5/2009 | Hempel | A61B 6/032 378/145 |
| 7,564,941 B2 * | 7/2009 | Baumann | A61B 6/484 378/146 |
| 7,639,786 B2 * | 12/2009 | Baumann | A61B 6/484 378/145 |
| 7,646,843 B2 * | 1/2010 | Popescu | A61B 6/032 356/521 |
| 7,746,981 B2 | 6/2010 | Takahashi | |
| 7,945,018 B2 | 5/2011 | Heismann et al. | |
| 7,983,381 B2 * | 7/2011 | David | A61B 6/032 378/4 |
| 8,009,892 B2 | 8/2011 | Ohara et al. | |
| 8,041,004 B2 | 10/2011 | David et al. | |
| 8,073,099 B2 * | 12/2011 | Niu | A61B 6/00 378/36 |
| 8,184,771 B2 * | 5/2012 | Murakoshi | G01N 23/20075 378/145 |
| 8,391,581 B2 | 3/2013 | Masuda et al. | |
| 8,451,975 B2 * | 5/2013 | Tada | A61B 6/4291 378/207 |
| 8,576,983 B2 | 11/2013 | Baeumer et al. | |
| 8,767,916 B2 * | 7/2014 | Hashimoto | A61B 6/484 378/62 |
| 9,066,649 B2 * | 6/2015 | Roessl | A61B 6/00 |
| 2010/0091947 A1 | 4/2010 | Niu et al. | |
| 2010/0246765 A1 | 9/2010 | Murakoshi et al. | |
| 2011/0243302 A1 | 10/2011 | Murakoshi | |

FOREIGN PATENT DOCUMENTS

| | | |
|---|---|---|
| CN | 101129266 A | 2/2008 |
| CN | 101960296 A | 1/2011 |
| DE | 102006017290 A1 | 8/2007 |
| EP | 1463085 A2 | 9/2004 |
| EP | 1879020 A1 | 1/2008 |
| WO | 2009101569 A2 | 8/2009 |

OTHER PUBLICATIONS

Single grating method for low dose 1-D and 2-D phase contrast X-ray imaging F. Krejci, J. Jakubek and M. Kroupa 2011 IOP Publishing Ltd and SISSA; 2011; CZ; Jan. 11, 2011.

Hard x-ray phase contrast imaging using single absorption grating and hybrid semiconductor pixel detector Frantisek Krejci, Jan Jakubek and Martin Kroupa Review of Scientific Instruments 81 113702 (2010); 2010; CZ; Nov. 5, 2010.

Quantitative x-ray phase-contrast imaging using a single grating of comparable pitch to sample feature size Kaye S. Morgan, David M. Paganin and K.W. Siu Optics Letters vol. 36 No. 1; 2011; AU; Jan. 1, 2011.

Fast X-Ray Phase-Contrast Imaging Using High Resolution Detector Zhentian Wang, Zhifeng Huang, Li Zhang, Kejun Kang and Peiping Zhu IEEE Transactions on nuclear science vol. 56, No. 3; 2009.

* cited by examiner

X-RAY DETECTOR OF A GRATING-BASED PHASE CONTRAST X-RAY DEVICE AND METHOD FOR OPERATING A GRATING-BASED PHASE CONTRAST X-RAY DEVICE

BACKGROUND OF THE INVENTION

Field of the Invention

The present invention relates to an x-ray detector of a grating-based phase contrast x-ray device, wherein, in particular, the x-ray detector can be used to determine the phase of an x-ray beam interference pattern. The invention furthermore relates to a method for operating such a grating-based phase contrast x-ray device.

Conventional x-ray devices for imaging by means of x-ray beam absorption are based on the fact that strongly absorbing body parts, such as e.g. bones, provide a high contrast in x-ray imaging compared to weakly absorbing body parts, such as e.g. tissue. However, if imaging of various body parts which all have a small x-ray beam absorption cross section is desired, conventional x-ray devices for imaging by means of x-ray beam absorption reach their limits due to a low signal-to-noise ratio. By way of example, this is the case if imaging of different types of tissue is desired, as may occur in mammography or angiography.

In such cases, grating-based phase contrast x-ray imaging can generate a higher contrast between the various body parts, such as e.g. between various tissue types. EP 1 879 020 A1 discloses an x-ray beam interferometer for obtaining quantitative x-ray beam images by means of grating-based phase contrast x-ray imaging. The interferometer comprises an x-ray beam source, a source grating, an object, a phase grating, an absorption grating and an x-ray detector. The periodicity of the phase grating and of the absorption grating lies in the region of $10^{-6}$ meters. By contrast, the spatial resolution of the x-ray detector is generally substantially lower. The spatial resolution of a detector is typically proportional to the distance between neighboring detector elements or pixels. In particular, the x-ray detector is unable to resolve directly the interference pattern which is caused by the arrangement of the phase grating in the beam path of the x-ray beams.

To this end, use is made of the absorption grating: minima or maxima of the interference pattern caused by the phase grating are selectively shadowed. The signal intensity detected by the x-ray detector therefore depends on the position of the absorption grating in relation to the minima and maxima of the intensity of the x-ray beams of the interference pattern of the phase grating. The introduction of an absorption grating into the beam path of the x-ray beams brings about absorption of approximately 50% of the x-ray beams. This reduces the effectiveness of the measurement or the radiation exposure is increased.

The distance between the minima and maxima of the interference pattern of the phase grating is only a few micrometers, i.e., it lies in the same order of magnitude as the periodicity of the phase grating. It is therefore necessary to position the absorption grating in the beam path of the x-ray beams with the same accuracy. However, positioning with micrometer accuracy requires much design and maintenance outlay, which is why the design and operation of such a grating-based phase contrast x-ray interferometer are expensive. Moreover, a very significant amount of time is required for positioning the absorption grating in the beam path of the x-ray beams compared to the actual measurement time. This lengthens the measurement in an undesirable manner.

In particular, it may be desirable to use the same x-ray device both for grating-based phase contrast x-ray imaging and for conventional absorption x-ray imaging. In order to ensure this, it is necessary to be able to introduce both the phase grating and the absorption grating into the beam path of the x-ray beams and to be able to remove these again when a switch is made between the two modes of operation. This causes, firstly, large local displacement paths and, secondly, very precise positioning in the micrometer range to become necessary for the absorption grating. These two inherently conflicting requirements further increase the design and maintenance costs.

An option for providing an improved x-ray detector for grating-based phase contrast x-ray imaging would lie in increasing the spatial resolution of the detector to the extent that the minima and maxima of the interference pattern caused by the phase grating can be resolved directly and it therefore being possible to dispense with the absorption grating. X-ray detectors with such a high spatial resolution have only been available for a short time. However, it is not possible to use these x-ray detectors directly in conjunction with an x-ray detector for grating-based phase contrast x-ray imaging since such detectors with high spatial resolution have a particularly low sensitivity to x-ray beams. It is possible that the sensitivity per detector area remains the same. At the same time, the pixel size is reduced when the spatial resolution is increased, and so fewer x-ray quanta are detected per detector pixel. In order to obtain a sufficient signal amplitude, the x-ray dose would have to be increased accordingly. This is undesirable, for example due to radiation protection legislation and the known negative implications of x-rays in the human body.

BRIEF SUMMARY OF THE INVENTION

It is therefore an object of the present invention to provide an improved x-ray detector of a grating-based phase contrast x-ray device, which, in particular, makes do without absorption grating and has a high sensitivity or has a greatly reduced radiation exposure. It is furthermore an object of the present invention to provide a method for operating a grating-based phase contrast x-ray device which comprises such an improved x-ray detector.

It is furthermore an object of the present invention to provide a method for operating an x-ray device with an x-ray detector, which comprises a first and a second mode of operation, wherein, in accordance with the first mode of operation, the x-ray device is operated as grating-based phase contrast x-ray device and, in accordance with the second mode of operation, as absorption x-ray device.

These objects are achieved by the features of the independent patent claims. The dependent claims describe preferred embodiments of the invention.

In accordance with a first aspect of the invention, an x-ray detector is provided, which comprises detector elements for recording signal values belonging to an x-ray signal, wherein the detector elements are arranged in a two-dimensional manner in a detector plane. Here, in said detector plane, the detector elements provide a first spatial resolution in a first direction and a second spatial resolution in a second direction, which is orthogonal to the first direction.

The x-ray detector in accordance with the present invention furthermore comprises a combination element for combining the signal values from detector elements, belonging to one of at least two detector element groups, to form a group signal value, wherein at least two detector elements along the first direction belong to each detector element group.

The x-ray detector of the present invention furthermore comprises an image computing unit for calculating a spatially resolved image of an x-ray beam phase value, wherein the image computing unit calculates an x-ray beam phase value from, in each case, at least three group signal values.

Typically, at least parts of x-ray detectors are produced in mainly two-dimensionally effective lithographic methods using semiconductor materials. Therefore, the arrangement of the detector elements typically takes place in a plane in a matrix structure. When x-ray beams impinge on a detector element, this detector element generates a signal in the form of e.g. a voltage pulse. The associated signal value can, for example, be proportional to the intensity or amplitude of the incident x-ray radiation.

Since every group signal value generated in the combination element emerges from the combination of at least two signal values from individual detector elements, the group signal value in accordance with the present invention is greater than the individual signal values of the individual detector elements. The group signal value has a greater distance from a noise level considered to be constant in the following. The signal-to-noise ratio of the group signal value is greater than the signal-to-noise ratio of the signal values of individual detector elements. This is advantageous, particularly in x-ray imaging, because, in the case of an unchanging signal-to-noise ratio, it is possible either to select a lower x-ray beam dose or to obtain an image with a higher signal-to-noise ratio in the case of an unchanging x-ray beam dose.

In particular, in accordance with the present invention, it is possible to dispense with the use of an absorption grating. Placing an absorption grating into the beam path of the x-ray beams causes a significant fraction of the x-ray beams to be absorbed prior to reaching the detector plane. A conventional x-ray detector of a grating-based phase contrast x-ray device using an absorption grating therefore, compared to the present invention, has an inherently reduced signal value used to calculate the x-ray beam phase value since a significant portion of approximately 50% of the x-ray beams is always absorbed in the absorption grating. Thus, according to the invention, it is possible to reduce the required x-ray beam dose compared to the prior art, while the signal-to-noise ratio remains unchanged.

The x-ray detector can comprise a phase grating, which is arranged in the beam path of the x-ray beams upstream of the detector plane and has a periodicity along the first direction. In phase contrast x-ray imaging, the phase grating causes the formation of an x-ray beam interference pattern in the beam path downstream of the phase grating. The x-ray detector is arranged there. The x-ray beam phase value in accordance with grating-based phase contrast x-ray imaging can be calculated from the local phase of the x-ray beam interference pattern. To this end, it is necessary to determine the position of the minima/maxima of the x-ray beam interference pattern.

The image computing unit of the present invention can, for example, calculate this x-ray beam phase value from, in each case, at least three group signal values. The grating periodicity of the phase grating is typically in the region of $10^{-6}$ meters, for example in the range from 1 to 20 micrometers. The periodic signal required by the image computing unit for calculating the x-ray beam phase value has a periodicity of the same order of magnitude.

In order to determine an x-ray beam phase value uniquely and precisely, the image computing unit can use at least three, preferably four, group signal values on the length of a periodicity of the x-ray beam interference pattern. This means that the first spatial resolution which is provided by the x-ray detector must be able to resolve features which are significantly smaller, for example by a factor of three to ten, than the periodicity of the phase grating. Thus, if the periodicity of the phase grating lies in the range from 1 to 20 micrometers, the first spatial resolution of the x-ray detector in accordance with the present invention should provide a spatial resolution which is approximately 0.25 to 5 micrometers. Only then is the image computing unit able to calculate the x-ray beam phase values uniquely and precisely.

In the case of such low spatial resolutions, the sensitivity of the x-ray detector typically reduces drastically and significantly. X-ray signals with the same amplitude now only generate a lower signal value. If the measurement is to be carried out with an unchanging signal-to-noise ratio, the x-ray beam dose has to be increased accordingly. Often this is undesirable.

An advantage of the present invention lies in combining a plurality of signal values from individual detector elements to form a group signal value, which, as a result thereof, has a higher signal value.

According to the present invention, the signal values of those detector elements are preferably combined, which are grouped on the basis of the criterion of the grating periodicity of the phase grating. The periodicity of the phase grating decisively determines the periodicity of the interference pattern of the x-ray beams in the detector plane. If the periodicity of the phase grating is known, it is possible, for example by calculation, to deduce the periodicity of the signal within the detector plane.

This is advantageous in that, due to the knowledge of the periodicity of the x-ray beam interference signal, skillful combination of signal values to form group signal values leads to the group signal value having a signal-to-noise ratio which is sufficient to calculate an image of the x-ray beam phase value in the case of a comparatively low x-ray beam dose. According to the present invention, it is advantageous if the combination element combines the signal values from detector elements of a detector element group, in which the distance between two mutually closest detector elements of the same detector element group is equal to an integer multiple of a local periodicity of the x-ray signal. The distance between two mutually closest detector elements of the same detector element group along the first direction should, in the following, define a detector element evaluation distance.

In accordance with this embodiment of the present invention, the detector element evaluation distance equaling an integer multiple of the local periodicity of the x-ray signal ensures that the respectively combined signal values relate to the same phase of the x-ray beam interference pattern and therefore have the same values. By way of example, only signal values of detector elements of one detector element group which correspond to the interference maxima or interference minima of the x-ray beam interference pattern are combined in the combination element. However, in particular, signal values which correspond to both the interference maxima and the interference minima are not combined. This is always the case if the detector element evaluation distance equals an integer multiple of the local periodicity of the x-ray signal. The detector elements of a detector element group are then situated at local positions at which the x-ray beam interference pattern in the unperturbed state, i.e. without object in the beam path of the x-ray beams, have the same phase.

In particular, the detector element evaluation distance can equal half the periodicity of the phase grating. The periodicity of the phase grating determines the periodicity of the x-ray beam interference pattern. At a specific distance behind the phase grating, the periodicity of the x-ray beam interference pattern typically is half the periodicity of the phase grating. If the detector plane is situated at this specific distance in the beam path of the x-ray beams downstream of the phase grating and if the detector element evaluation distance is set to equal half the periodicity of the phase grating, the detector element evaluation distance corresponds to the local periodicity of the x-ray signal or of the x-ray beam interference pattern.

An image of the x-ray beam phase value can be calculated from the group signal value in the image computing unit. Preferably, this is brought about in such a way that, to calculate the x-ray beam phase value, the image computing unit assigns to the at least three group signal values a relative distance from one another and calculates a trigonometric function described by the x-ray beam phase value, which function describes the group signal value as a function of the relative distance and hence the x-ray beam phase value.

Here, the first spatial resolution and hence typically the distance between neighboring detector elements is down to the design and therefore a fixed property of the x-ray detector. If the combination element combines individual signal values of detector elements and forms group signal values therefrom, a relative distance from one another can be assigned to the individual group signal values on the basis of the distance of adjacent detector elements, which is down to design and therefore known.

By way of example, if detector elements numbered one, four, seven (wherein the detector elements are numbered along the first direction) belong to a first detector element group, the detector elements numbered two, five, eight, for example, belong to a second detector element group and, finally, a third detector element group has detector elements numbered three, six, nine, the assigned relative distance is in each case the distance between neighboring detector elements, for example the distance between detector element number one and two, or two and three. This is equivalent to scanning the interference pattern by group signal values within a period of the x-ray beam interference pattern. The local profile of the x-ray beam interference pattern can be described physically by a trigonometric function, for example a sine or cosine function. The exact parameters of the trigonometric function, for example amplitude and phase, and also periodicity, can be calculated if at least three values within one period of the trigonometric function are available. The parameter of the phase of the trigonometric function describes the x-ray beam phase value in this case.

In accordance with the described embodiment of the present invention, the image computing unit can adapt the trigonometric function to the at least three group signal values in such a way that the trigonometric function describes the measured signal profile to the best possible extent. In order to adapt functions to measured values, a number of different methods are known in the literature.

The calculation of the x-ray beam phase value becomes ever more accurate in this case as ever more group signal values are used by the image computing unit for calculation. Furthermore, the calculation of the x-ray beam phase value becomes ever more accurate, the more accurately the individual group signal values are known. If the measured group signal values are afflicted with large errors, the calculation of the x-ray beam phase value can also be afflicted by a comparatively large uncertainty. By contrast, if every group signal value is known with great certainty, the error in the calculation of the x-ray beam phase value will also be comparatively small.

Since an x-ray beam phase value is calculated from at least three group signal values, the local image of the x-ray beam phase value calculated by the image computing unit can have an image resolution which is lower than the first spatial resolution. Here, the image resolution can denote a spatial resolution of the image, which emerges from the actual distance between two objects imaged by neighboring pixels. The high spatial resolution of the detector is in this case advantageously used to calculate the x-ray beam phase value accurately. However, since several group signal values are used to calculate a pixel of the image, for example by combining the signal values of three or four detector elements, the image of the x-ray beam phase value may have a lower image resolution.

Furthermore, the detector element evaluation distance can be greater than the first spatial resolution. In particular, the distance between two neighboring detector elements along the first direction can define the first spatial resolution. If the detector element evaluation distance is greater than the first spatial resolution, then it can also be greater than the distance between two neighboring detector elements along the first direction.

In particular, for example, in the case of a strictly periodic arrangement of detector elements along the first direction, no feature which is smaller than the distance between two neighboring detector elements can be resolved in the image anymore. Accordingly, the first spatial resolution is less than the distance between two neighboring detector elements. A person skilled in the art knows of different definitions of the spatial resolution in relation to the distance between neighboring detector elements. This will not be discussed in any more detail in the following.

The distance between two neighboring detector elements along the first direction can equal a quotient of integers of the local periodicity of the x-ray signal. If this is the case, this ensures that the arrangement of the detector elements in the x-ray detector is commensurable with the local periodicity of the x-ray signal. In other words: if the distance between two neighboring detector elements is commensurable with the local periodicity of the x-ray signal, it is always possible to find a detector element evaluation distance which equals the local periodicity of the x-ray signal (and is not only equal to an integer multiple of the local periodicity of the x-ray signal).

By way of example, if the distance between two neighboring detector elements equals a quarter of the local periodicity of the x-ray signal, it is possible to achieve the following by combining the signal values of the first, fifth, tenth etc. detector element arranged along the first direction to form a first group signal value, the signal values of the second, sixth, eleventh etc. signal element to form a second group signal value, the third, seventh, twelfth signal value to form a third group signal value and the fourth, ninth, fourteenth signal value to form a fourth group signal value: firstly, four group signal values can be provided by the image calculating unit within one periodicity of the x-ray signal for calculating the x-ray beam phase value. Secondly, every detector element can, in particular, be used for the combination by the combination element for the purposes of forming a group signal value. The present detector elements are therefore employed in an optimum manner since each detector element is assigned to a detector element group. The x-ray beam phase value can be determined with the greatest possible accuracy. However, it should be clear that it is not mandatory to provide four detector elements within one signal period or that not all detector elements need to belong to detector element groups.

In order to ensure that the distance between two neighboring detector elements along the first direction equals a quotient of integers of the local periodicity of the x-ray signal, it is possible in each case to adapt parameters of the periodicity of the phase grating, the distance of the phase grating from the detector plane, the type and the arrangement of the x-ray beam source or the distance of neighboring detector elements or the first spatial resolution. By way of example, care can be taken when producing the detector that the distance between two neighboring detector elements in the complete detector is commensurable to the local periodicity of the x-ray signal. In the case of small deviations between the local periodicity of the x-ray signal and the distance between neighboring detector elements, it would furthermore be possible to vary the distance between the phase grating and the detector plane.

The detector element evaluation distance can preferably equal the local periodicity of the x-ray signal. By way of example, if the arrangement of the detector elements in the x-ray detector is commensurable with the local periodicity of the x-ray signal, one signal value of an associated detector element is taken from each period of the x-ray beam interference pattern in order to form a group signal value. This means that the local extent of the detector elements of a detector element group can be minimized (in the case of a fixed number of detector elements per detector element group). It follows from this that the image resolution of the local image can be maximized. This is the case because the image resolution is substantially determined by the local extent of the detector elements belonging to a detector element group.

In accordance with a further embodiment of the present invention, the combination element combines the signal values from detector elements in such a way that neighboring detector elements belong to different detector element groups. In particular, it is advantageous if, to form the group signal values, the knowledge in respect of the periodicity of the x-ray signal is employed in such a way that signal values of neighboring detector elements are not combined. If signal values of non-neighboring detector elements are combined along the first direction, use is advantageously made of the high spatial resolution of the detector and the knowledge about the signal periodicity of the x-ray signal in order to calculate the x-ray beam phase value. According to the invention, this permits a particularly accurate determination of the x-ray beam phase value at a low signal dose.

In accordance with one embodiment of the present invention, the combination element sums signal values from detector elements. By summing signal values from detector elements to form group signal values, the group signal value increases linearly with the number of detector elements. The assumption can then be made that, for example, in the case where five summed signal values form one group signal value, the image has a signal-to-noise ratio which is higher by a factor of five than the signal-to-noise ratio of an image calculated from individual signal values. Other options for combining the signal values of detector elements to form group signal values would include multiplication, division or logarithmic addition. This list is in no way restrictive. Other options for combining signal values to form group signal values are known in the literature and can, according to the invention, be used to form group signal values.

In accordance with one preferred embodiment, the combination element only combines the signal values from detector elements which are arranged along the first direction. In particular, as a result of this, detector elements which have different positions in the detector plane along the second direction always belong to different detector element groups.

In accordance with a further embodiment, the first spatial resolution is higher than the second spatial resolution. By way of example, this is the case if the extent and hence the distance of neighboring detector elements along the first direction is less than the extent and hence the distance of the detector elements along the second direction. By way of example, the detector elements may have a dimension of 4 micrometers or less along the first direction but have a dimension of 85 micrometers or greater along the second direction. The detector elements then have a rectangular form in the detector plane. If the detector elements are arranged as tightly as possible in the detector plane according to the stipulation of the aforementioned dimensions, the first spatial resolution is accordingly higher than the second spatial resolution. In particular, the image resolutions of an image in the first and second direction can depend differently on respectively the first and second spatial resolution. In particular, it is also possible that the image resolution of the image is the same along the first and second direction.

The first spatial resolution is preferably able to resolve features down to 10 µm or down to 1 µm. This enables a determination of the image of the x-ray beam phase value with a sufficiently high image resolution.

In particular, the phase grating can be arranged in the beam path of the x-ray beams in such a way that it generates an interference pattern along the first direction in the detector plane, i.e. the grating periodicity is along the first direction. It can then be the case that no interference pattern is generated along the second direction in the detector plane. A high resolution in the grating-based phase contrast x-ray imaging can therefore inherently only be generated along the first direction. In other words, a change in the phase value in the form of the phase jumps can only be observed along the first direction. According to the invention, it is accordingly advantageous to design the second spatial resolution to be lower than the first spatial resolution and therefore increase the image quality of the image.

In accordance with a further embodiment of the present invention, the x-ray detector furthermore comprises a grouping member, which determines the number of detector elements belonging to a detector element group on the basis of at least one of the following criteria: image resolution of the image, signal intensity, time required to create the image. By way of example, if a large number of detector elements are combined to form a group signal value, changes in the x-ray beam phase value with a short characteristic length, i.e. many phase jumps per unit length, cannot be resolved. This is the case because the distance between the first and last detector element whose signal values are combined to form a group signal value, is greater than the characteristic length of the change in the x-ray beam phase value. In other words, the number of the signal values from detector elements combined to form a group signal value defines the image resolution of the spatially resolved image of the x-ray beam phase value which is calculated by the image computing unit. If many detector elements belong to a detector element group, the image resolution is low. The image resolution is correspondingly high if only a few signal values from detector elements are combined to form a group signal value.

If only a few signal values from detector elements are combined to form a group signal value, the image resolution of the image of the x-ray beam phase value increases but the group signal values simultaneously reduces. The group signal value must typically reach a certain value in order to ensure a resilient calculation of the x-ray beam phase value by the image computing unit. It may therefore be necessary to set the number of detector elements belonging to a detector element group on the basis of the signal intensity of the x-ray signal. If the signal intensity of the x-ray signal is high, it may be sufficient to combine the signal values of a few detector elements in order to form the sensed signal value. By contrast, if the signal intensity of the x-ray signal is low, for example because it is desirable to use a low x-ray beam dose, it is accordingly necessary for more signal values from detector elements to be combined to form a group signal value.

If the x-ray beam power, i.e. the amplitude of the x-ray radiation per time interval, is fixedly prescribed, the signal-to-noise ratio can also be increased by a longer exposure time with x-ray beams. By way of example, the x-ray beam dose can scale linearly with the duration of the exposure time: if the same object is exposed for approximately twice the time, the signal value also increases twofold. It is therefore possible that the duration for creating the image is material to the number of detector elements used to form a group signal value.

The grouping member can set the number of detector elements that belong to a detector element group. Since this number relates to the image resolution of the image of the x-ray beam phase value, the image resolution can be controlled accordingly. Compared to conventional grating-based phase contrast x-ray imaging, this furthermore has the advantage of flexibly adapting the image resolution. For example, if a high signal value is expected due to various measurement parameters, the image resolution can be increased accordingly. By contrast, if a low signal value (i.e. a low signal-to-noise ratio) is expected due to the various measurement parameters, the image resolution can be reduced, with, at the same time, the signal value and hence the signal-to-noise ratio being increased. This means that the x-ray beam dose can always be adapted optimally to the circumstances.

The image of the x-ray beam phase value can be calculated by the image computing unit from a single measurement. An advantage of this is that a particularly short period of time is required for the measurement. This enables a particularly efficient operation of an x-ray device in accordance with the present invention.

In particular, in the case of conventional grating-based phase contrast x-ray devices, it is necessary to displace the absorption grating a number of times and to carry out an x-ray image recording for each position of the absorption grating. For the unique and highly resolving determination of the x-ray beam phase value, it is conventionally necessary to carry out at least three, preferably four, recordings at different arrangements of the absorption grating. This results directly in an increase in the required x-ray beam dose and a lengthening of the measurement time duration. Accordingly, in accordance with the present invention, it is possible to reduce the x-ray beam dose and the measurement time duration.

At the same time, the obtained spatial resolution in accordance with the present invention can be increased by the use of only a single measurement. This will be described briefly in the following. When using several measurements to calculate an image of the x-ray beam phase value, the measurement necessarily extends over a relatively long measurement period of time. The longer the measurement period of time is, the more probable intermediate movements of the measurement object becomes. This is particularly the case in human diagnostics since it is difficult to keep the patient completely still over a relatively long period of time. In conventional grating-based phase contrast x-ray devices, it is necessary to extend the measurement period of time to such a length that the absorption grating can be displaced three or four times and the image recording can take place three or four times. The measurement period of time can therefore extend over several seconds or even minutes. If the patient moves during this measurement period of time, the positions of the individual images with respect to one another shift. Since such movements are not very deterministic, the image errors created by image displacement can only be corrected with much outlay.

The upshot of this is that the spatial resolution to be achieved in conventional grating-based phase contrast imaging is low in human-diagnostic questions.

The x-ray detector can be a CCD or a CMOS detector. Here, the detector elements can, in particular, be the pixels of the CCD or CMOS sensor. CCD sensors and CMOS sensors are known to a person skilled in the art as x-ray detector. Both methods are based on the use of semiconducting materials. The incidence of x-ray radiation is detected by means of an occurring voltage. The high-energy x-ray radiation is typically used first to generate low-energy radiation, which is then detected. Various advantageous embodiments of x-ray detectors are known to a person skilled in the art. This will not be discussed in any more detail in the following.

In accordance with one preferred embodiment, the periodicity of the phase grating is greater by at least a factor of six than features resolved in accordance with the first spatial resolution. In particular, the periodicity of the phase grating determines the periodicity of the x-ray signal in the detector plane or of the x-ray beam interference pattern. The distance between the phase grating and the detector plane can typically be selected in such a way that the periodicity of the x-ray beam interference pattern is shorter by a factor of two than the periodicity of the phase grating itself. Since at least three group signal values have to be present within one period of the x-ray beam interference pattern, in order to render it possible to calculate the spatially resolved image of the x-ray beam phase value precisely and uniquely in the image computing unit, it may be advantageous if the periodicity of the phase grating is greater than the first spatial resolution by a factor of six. Here, the factor of six is calculated from the factor of two from the relationship between periodicity of the phase grating—x-ray beam interference pattern multiplied by the factor of three for forming group signal values.

In accordance with a further aspect, the present invention furthermore provides a method for operating a grating-based phase contrast x-ray device and for evaluating signal values belonging to an x-ray signal from detector elements, which are arranged in a two-dimensional manner, of an x-ray detector, comprising the following steps:

capturing the signal values in each detector element,
combining the signal values from detector elements which, in each case, belong to one of at least two detector element groups to form group signal values, wherein the detector element groups are arranged along a spatial periodicity of the x-ray signal, which defines a first direction, in such a way that at least two detector elements belong to each group, wherein the distance between closest detector elements of a detector element group defines a detector element evaluation distance, which is greater than the distance between neighboring detector elements in the first direction,
calculating an image of an x-ray beam phase value, wherein an x-ray beam phase value is calculated from at least three group signal values.

This method in accordance with the present invention enables the operation of an x-ray detector for grating-based phase contrast x-ray imaging in accordance with the x-ray detector of a grating-based phase contrast x-ray device as described above.

By way of example, the method for operating a grating-based phase contrast x-ray device can furthermore comprise the following step: setting the detector element evaluation distance on the basis of the local periodicity of the x-ray signal. If the detector element evaluation distance is set within the scope of the method according to the invention for operating the grating-based x-ray device, this increases the flexibility. The detector element evaluation distance can respectively be set in a flexible manner in the case of a change in the local periodicity due to the measurement framework.

Accordingly, it is, for example, also possible to use different phase gratings for different measurement requirements. According to the method according to the invention, the detector element evaluation distance or the grouping of the detector elements is set on the basis of the modified periodicity of the phase grating. This brings about high flexibility when carrying out the measurement. Accordingly, the method can furthermore comprise the following step: setting the detector elements belonging to a group. If the detector elements belonging to a group (and hence the signal values from detector elements combined to form the group signal value) are set in each case, this can also increase the flexibility. Different measurement frameworks can require a different number or a different grouping of detector elements. By way of example, it may be advantageous to increase the signal-to-noise ratio for specific measurements, i.e. have more detector elements per detector element group.

Furthermore, the detector element evaluation distance can, for example, be set on the basis of a reference measurement. By way of example, if the periodicity of the phase grating is not known precisely or if various measurement parameters, such as e.g. the distance between the phase grating and the detector plane, change, it may be necessary first to determine the signal periodicity on the basis of a reference measurement. During a reference measurement, the introduction of an object into the beam path could be dispensed with. The detected signal then ideally has the same phase over the whole area of the detector. It is therefore particularly suitable for determining the detector element evaluation distance on the basis of the unperturbed periodicity of the signal.

Furthermore, within the scope of the reference measurement, it is possible for e.g. group signal values to be minimized or maximized as a function of the detector element evaluation distance. By way of example, if the detector element evaluation distance equals the periodicity of the signal, the group signal value, which corresponds to the detector elements arranged at the maxima of the periodic signal or of the x-ray beam interference pattern, will reach a maximum while the group signal value, which corresponds to the detector elements arranged at the minima of the x-ray beam interference pattern, will reach a minimum. By contrast, if the detector element evaluation distance does not correspond to the periodicity of the x-ray signal, signal values of detector elements which correspond to different phases of the signal are combined. There will therefore be neither a minimum nor a maximum group signal value since all group signal values have an averaged value. In other words, a minimization or maximization of different group signal values follows from the selection of the detector element evaluation distance equaling an integer multiple of the signal periodicity of the x-ray signal. This can be used as a criterion for determining the x-ray signal value within the scope of a reference measurement.

The belonging of the detector elements to detector element groups or the detector element evaluation distance can also be fixedly predetermined. An advantage of this is that there is no need for complicated evaluation electronics or calculation electronics for setting the detector element evaluation distance or the belonging of the detector elements to detector element groups. The costs for an instrument and the maintenance outlay are therefore reduced.

In accordance with a further aspect, the invention furthermore relates to a method for operating an x-ray device with an x-ray detector, which contains detector elements which are grouped and arranged in a two-dimensional manner in a detector plane, comprising a first mode of operation, for operating the x-ray device as grating-based phase contrast x-ray device as described above and a second mode of operation, for operating the x-ray device as absorption x-ray device.

This method according to the invention for operating an x-ray device provides the advantage of being able to switch the mode of operation of the x-ray device between conventional absorption x-ray imaging and grating-based phase contrast x-ray imaging in accordance with the present invention. Typically, phase contrast x-ray imaging is always used whenever conventional absorption x-ray imaging does not supply the desired signal value or the desired signal-to-noise ratio. Typical fields of application of phase contrast x-ray imaging include mammography or angiography. However, it may be advantageous to prefer absorption x-ray imaging instead of phase contrast x-ray imaging for imaging body parts with a high x-ray beam absorption contrast, such as e.g. bones or bone parts. Therefore, it is advantageous if the same x-ray device comprises a first and a second mode of operation, which enable both phase contrast x-ray imaging and absorption x-ray imaging. By way of example, this leads to cost reductions or simplified diagnosis conditions.

In conventional methods of phase-contrast imaging, a phase contrast and an absorption contrast image can be calculated automatically from the measurement values. However, an absorption grating is conventionally required, and so, at the same x-ray beam dose, the absorption image of a phase contrast measurement has a lower signal-to-noise ratio than an absorption image using a standard x-ray technique without absorption grating. According to the invention, a phase image, and a so-called dark-field image can be obtained in addition to the absorption image at the same dose.

According to one embodiment of the present invention, the second mode of operation comprises the following steps:
  capturing the signal values in each detector element,
  combining the signal values of grouped and mutually adjacent detector elements along a first direction in the detector plane to form group signal values,
  calculating a spatially resolved image of an x-ray beam absorption value, wherein an x-ray beam absorption value is calculated from, in each case, a group signal value. As discussed above, an x-ray detector according to the invention for the grating-based phase contrast x-ray device may contain detector elements which have small dimensions. This results in a low signal value of individual detector elements. The low signal value of detector elements of a detector with a high spatial resolution in accordance with the present invention can be compensated for by virtue of the fact that signal values of mutually neighboring detector elements are combined. In conventional absorption x-ray imaging, the signal to be detected does not have a periodicity, as is the case in grating-based phase contrast x-ray imaging. It is therefore advantageous in the second mode of operation to combine the signal values from detector elements neighboring one another.

The number of combined signal values can be set on the basis of one of the following criteria: image resolution of the image, time taken for creating the image. By way of example, if a large number of signal values of neighboring detector elements are combined to create the image, the image resolution of the image simultaneously reduces. On the other hand, the amplitude of the x-ray signal increases since several signal values of detector elements are combined. Accordingly, the duration for creating the image can be reduced since a lower x-ray beam dose per detector element is required to create the image.

In accordance with a preferred embodiment, the method for operating an x-ray device furthermore comprises a grouping step, for grouping the detector elements for subsequent combination in accordance with the first and second mode of operation. In each mode of operation, the detector elements can be grouped individually in such a way that the measurement parameters are adapted in an optimum fashion to the measurement object. Thus, as a result of the grouping step, it is possible to switch between the different modes of operation. While it may be necessary in the second mode of operation for operating the x-ray device for absorption x-ray imaging to group the signal values of neighboring detector elements, it may precisely be necessary in the first mode of operation not to group neighboring detector elements in one group.

BRIEF DESCRIPTION OF THE SEVEAL VIEWS OF THE DRAWING

Figure 2:
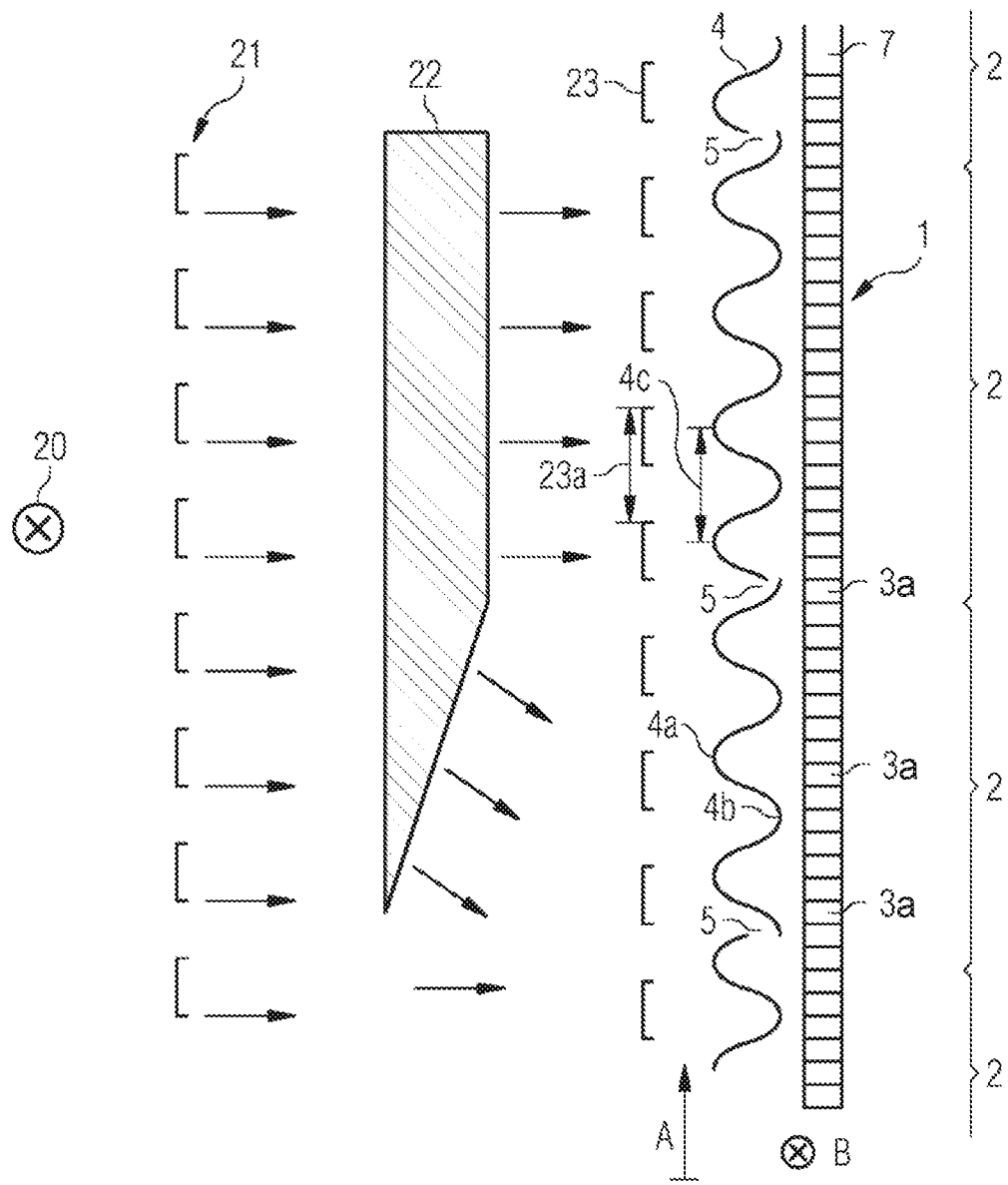
Figure 3:
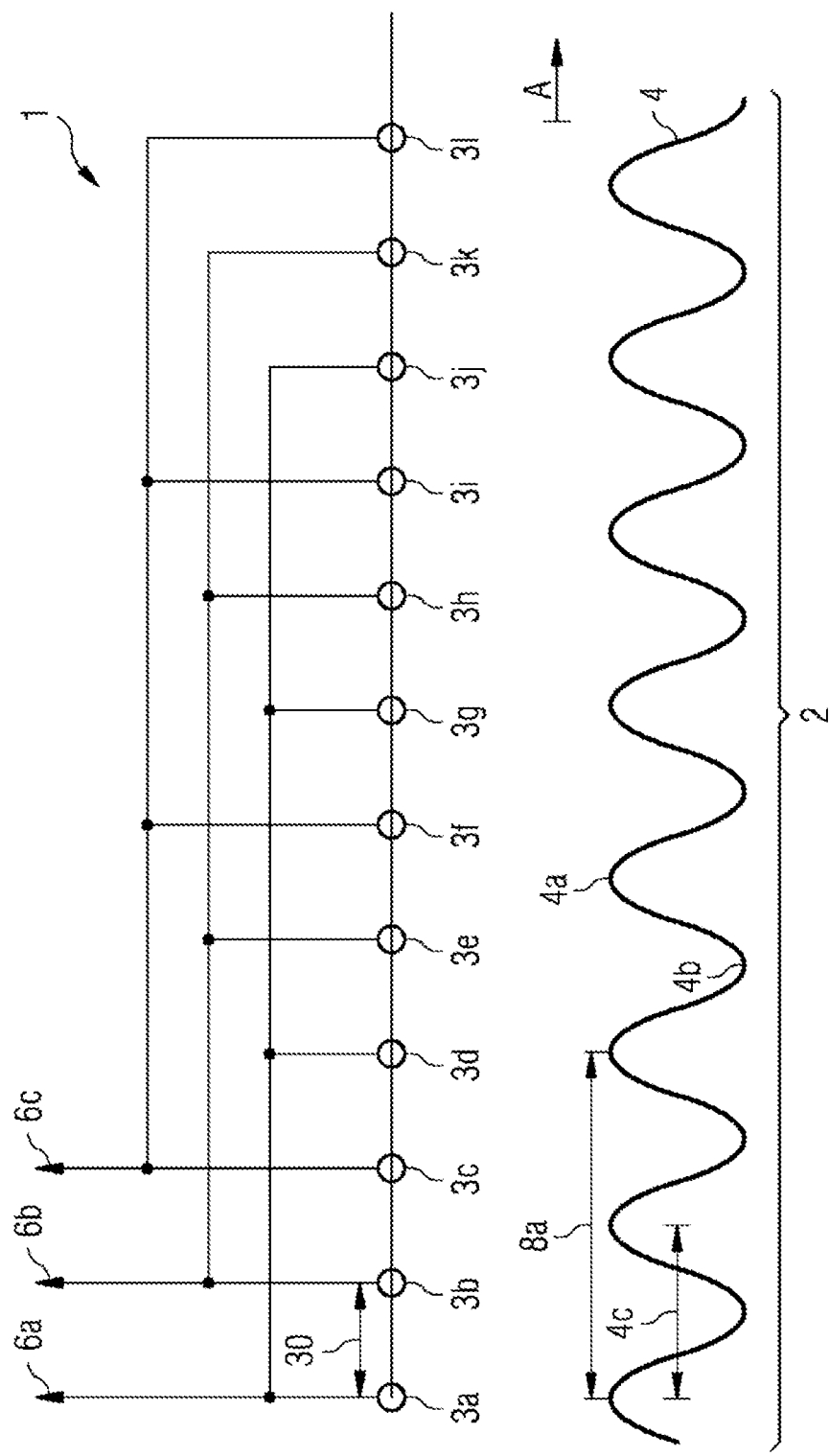
Figure 4:
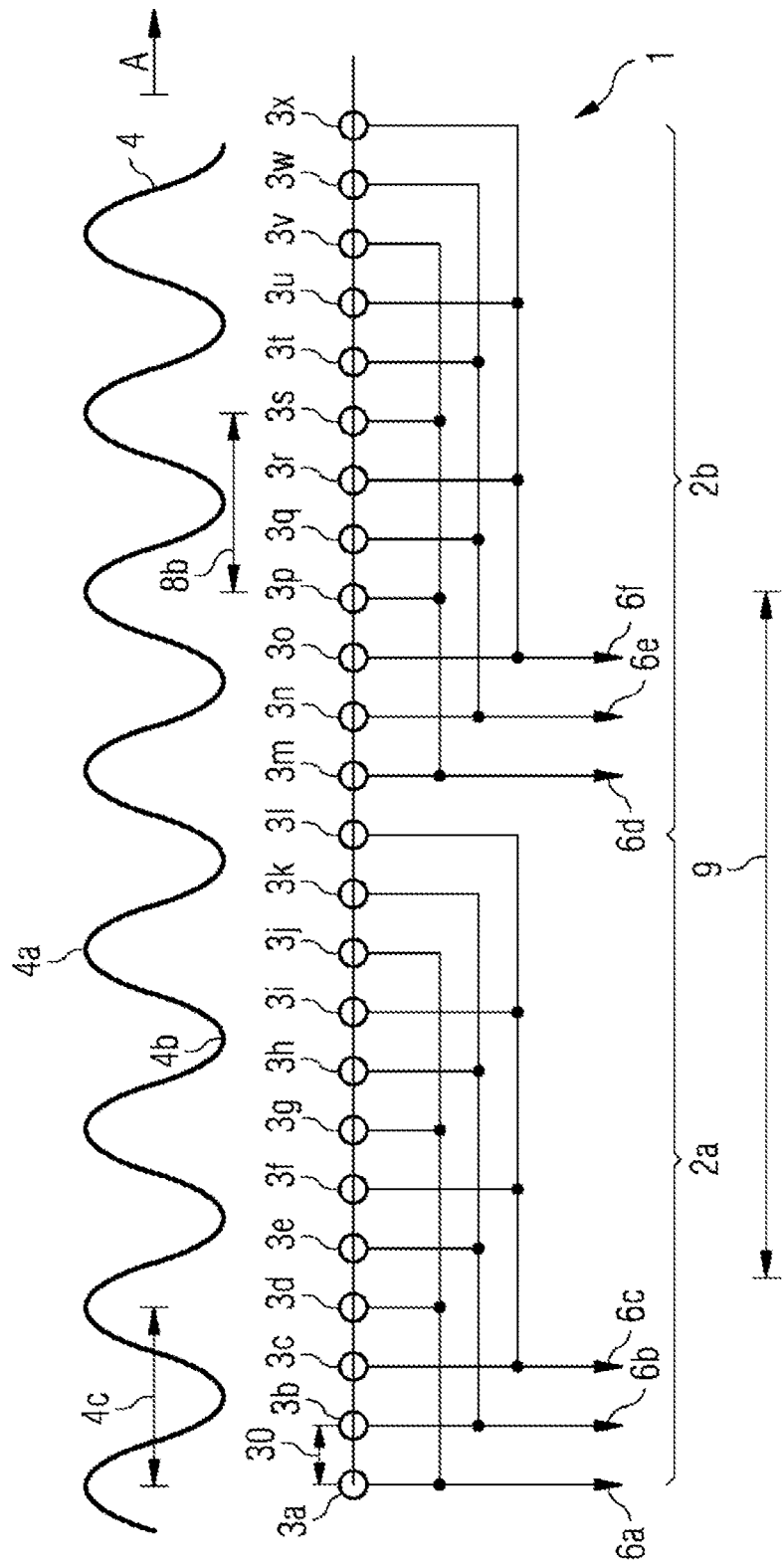
Figure 5:
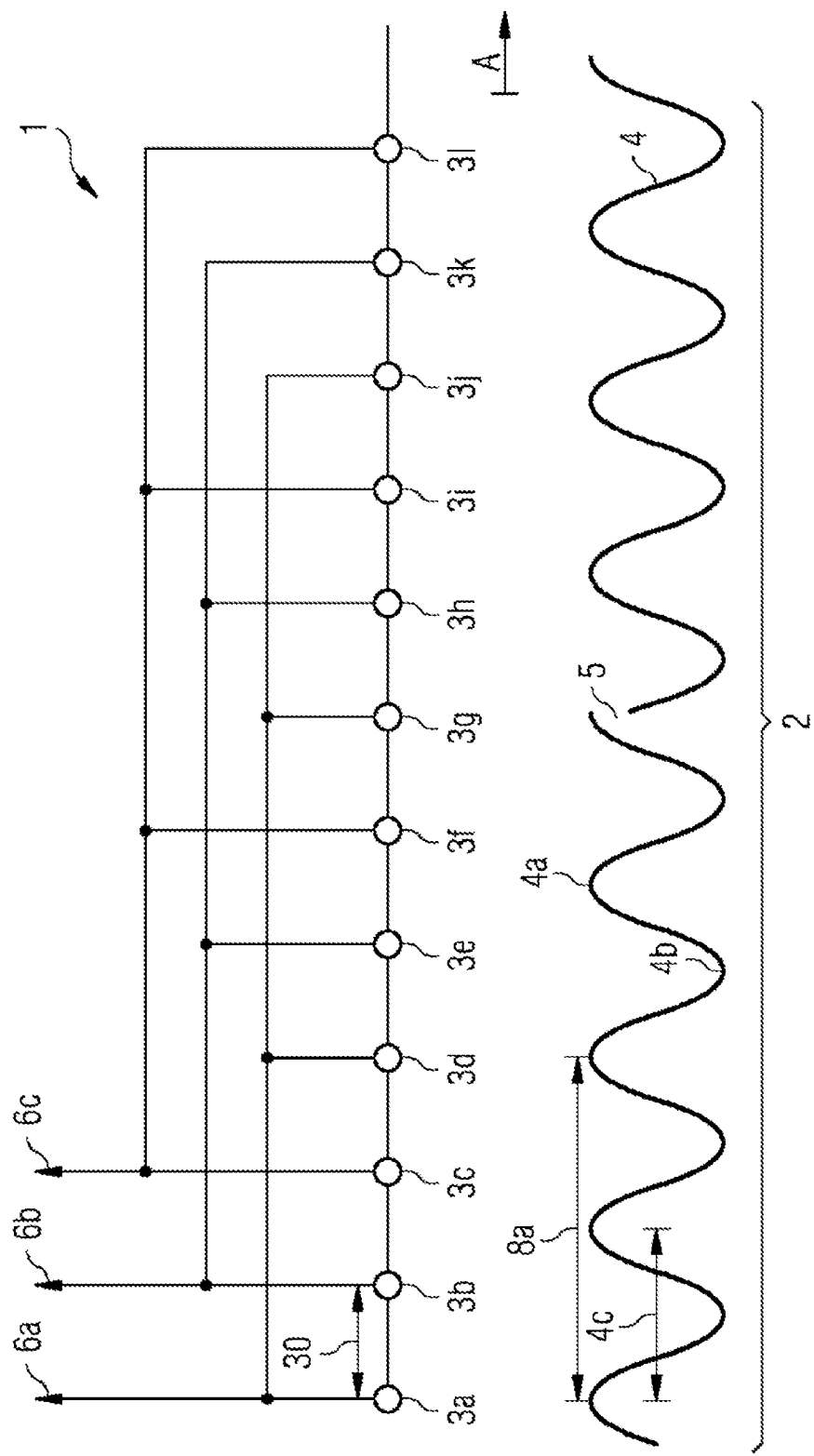
Figure 6:
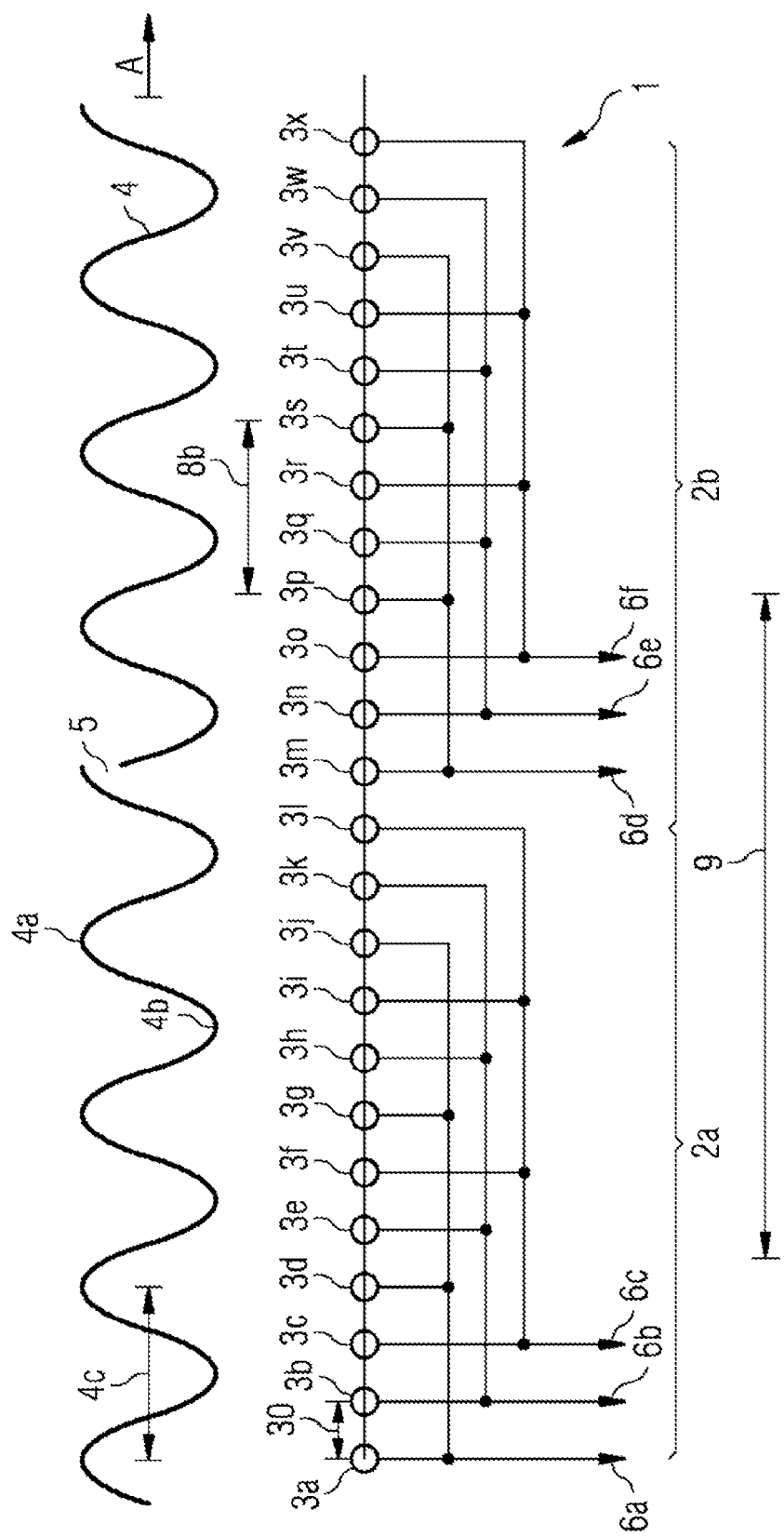
Figure 8:
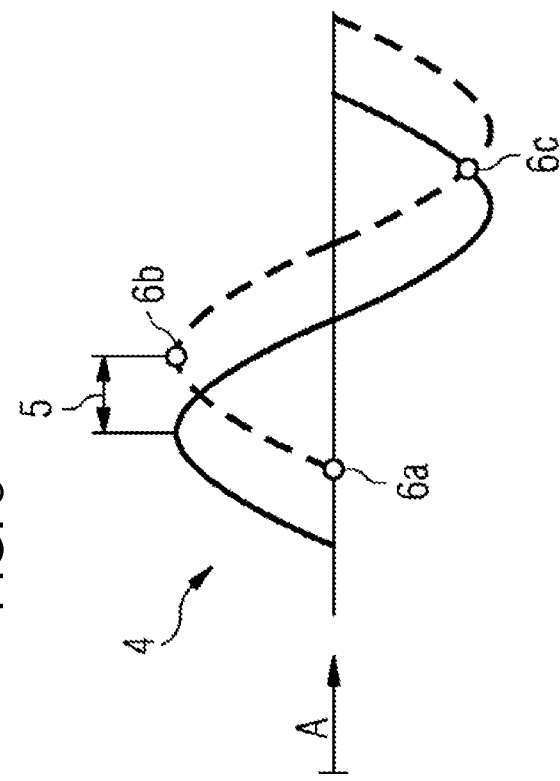
Figure 7:
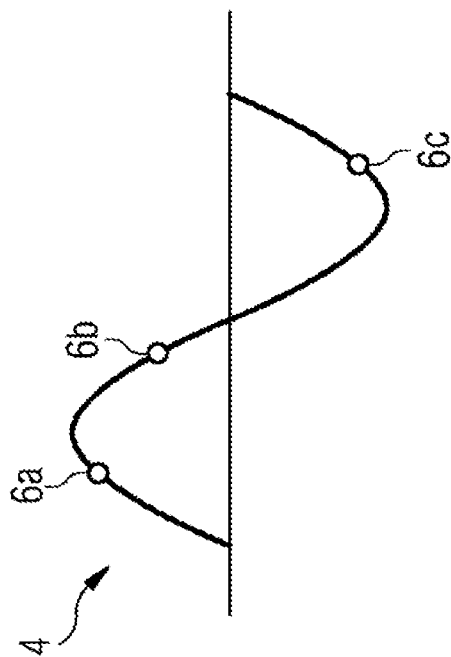
Figure 9:
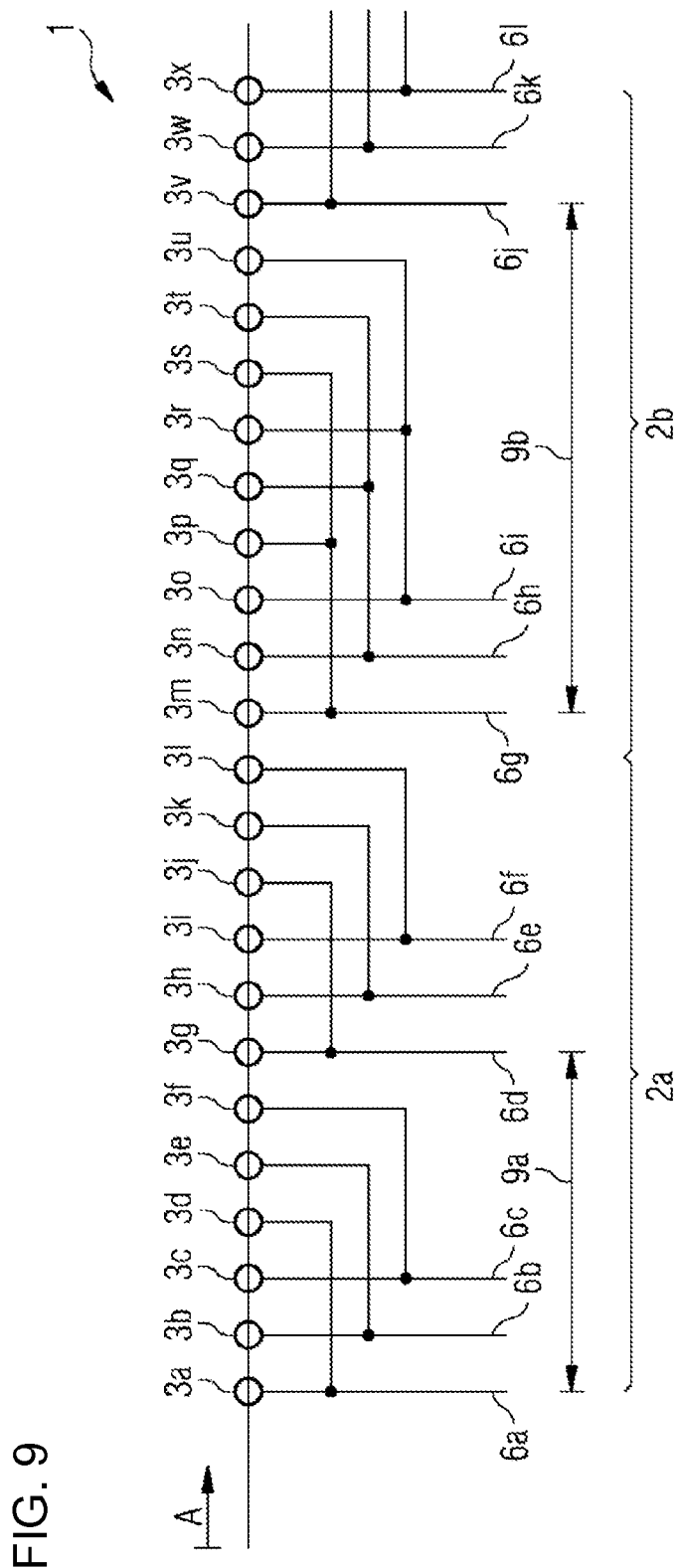
Figure 10:
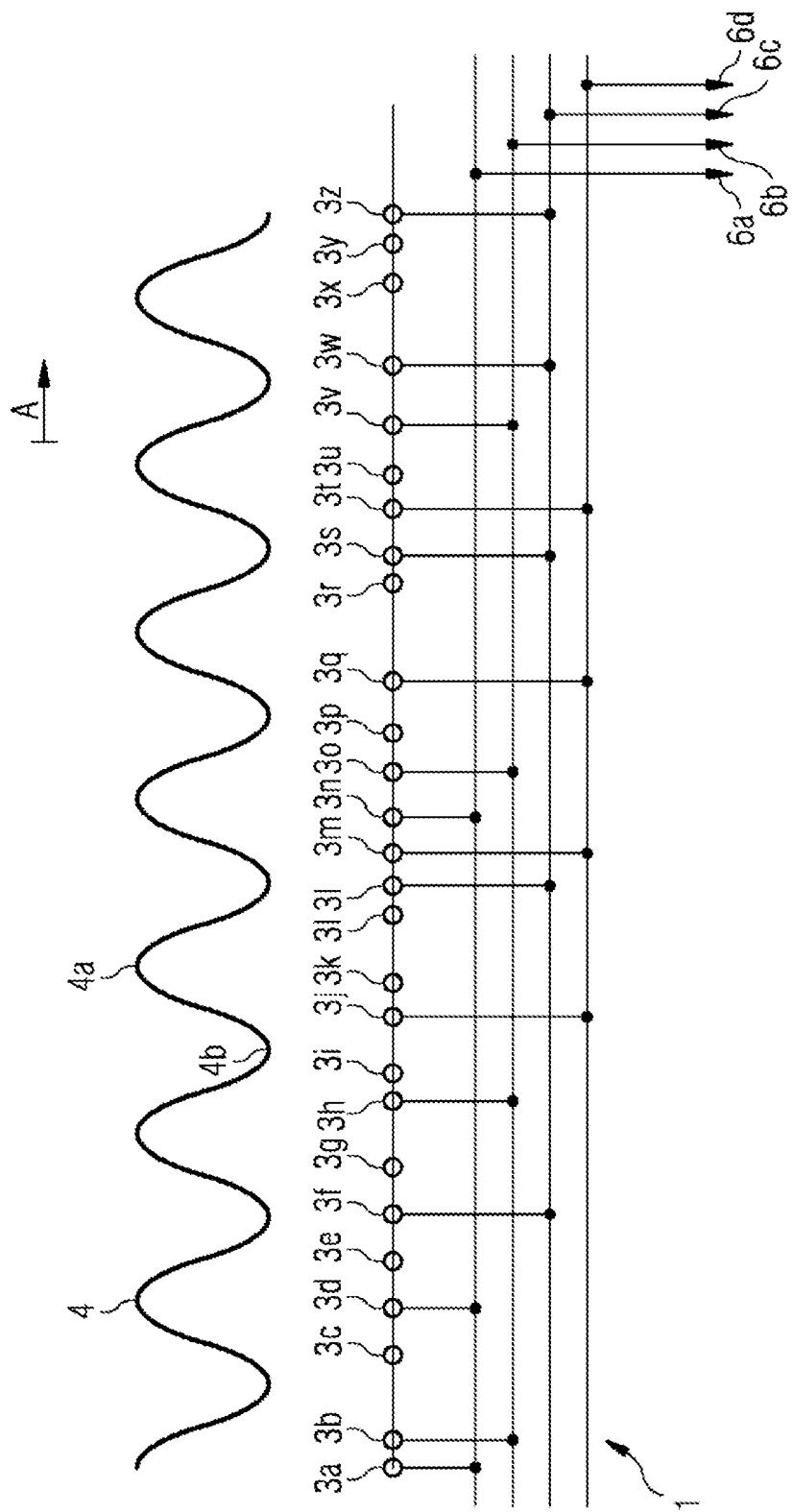
Figure 11:
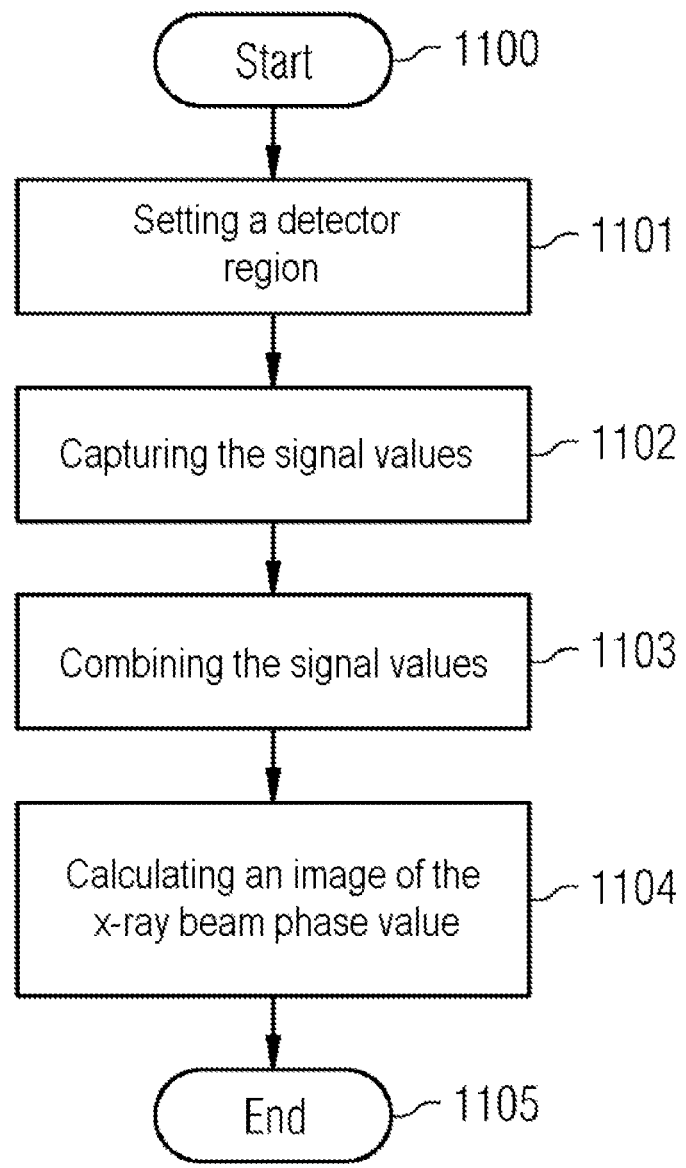
Figure 12:
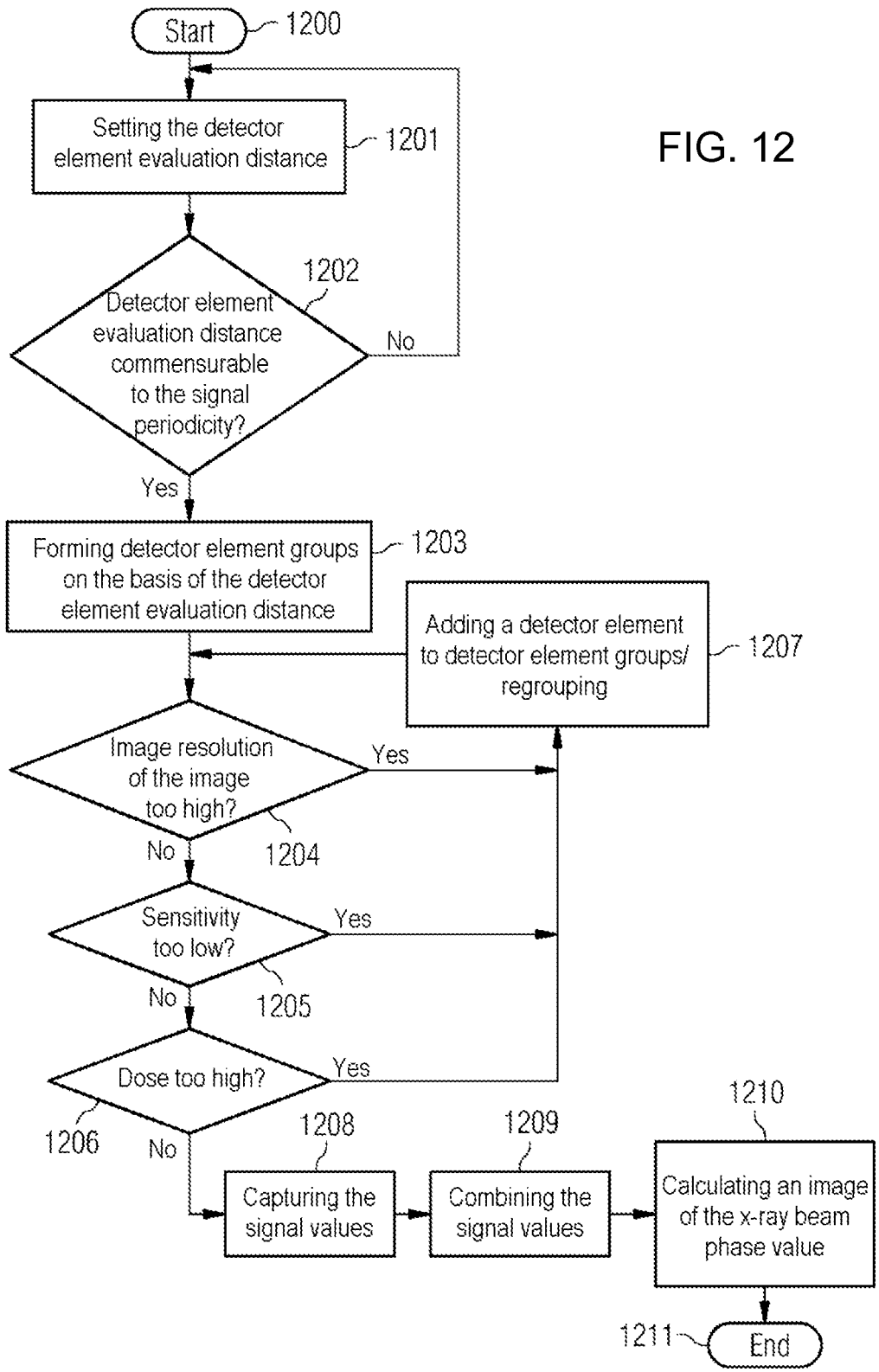
Figure 13:
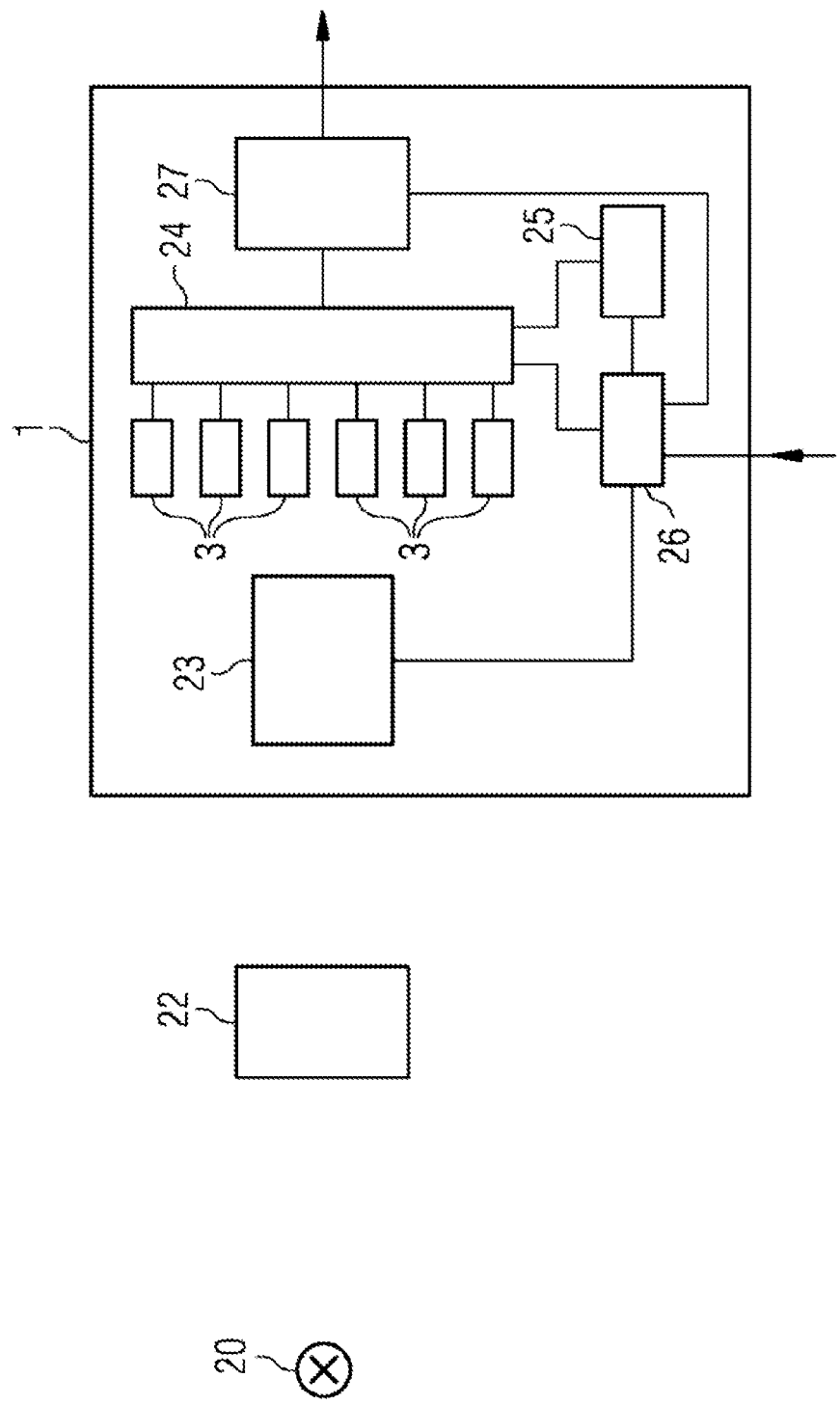
Figure 14:
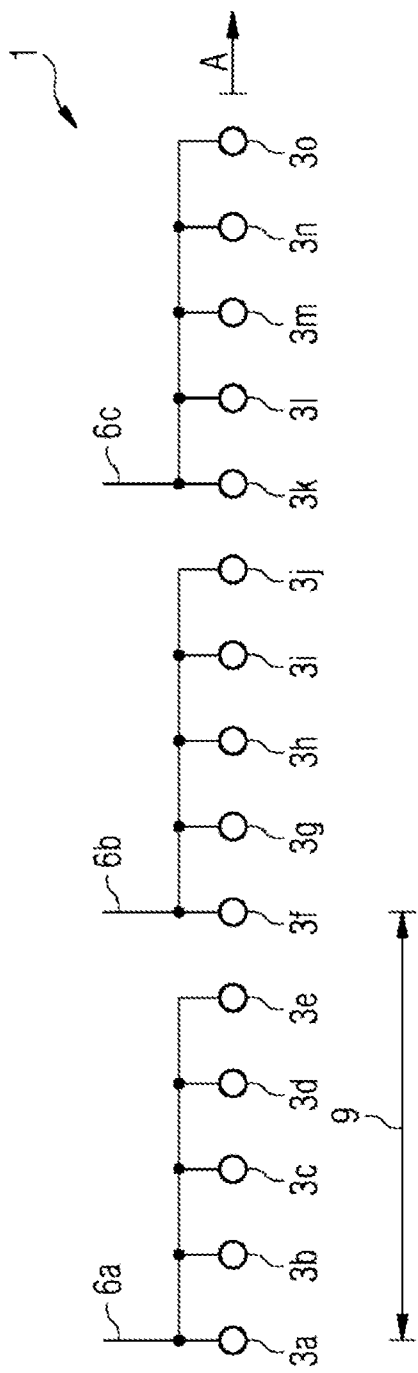
Figure 15:
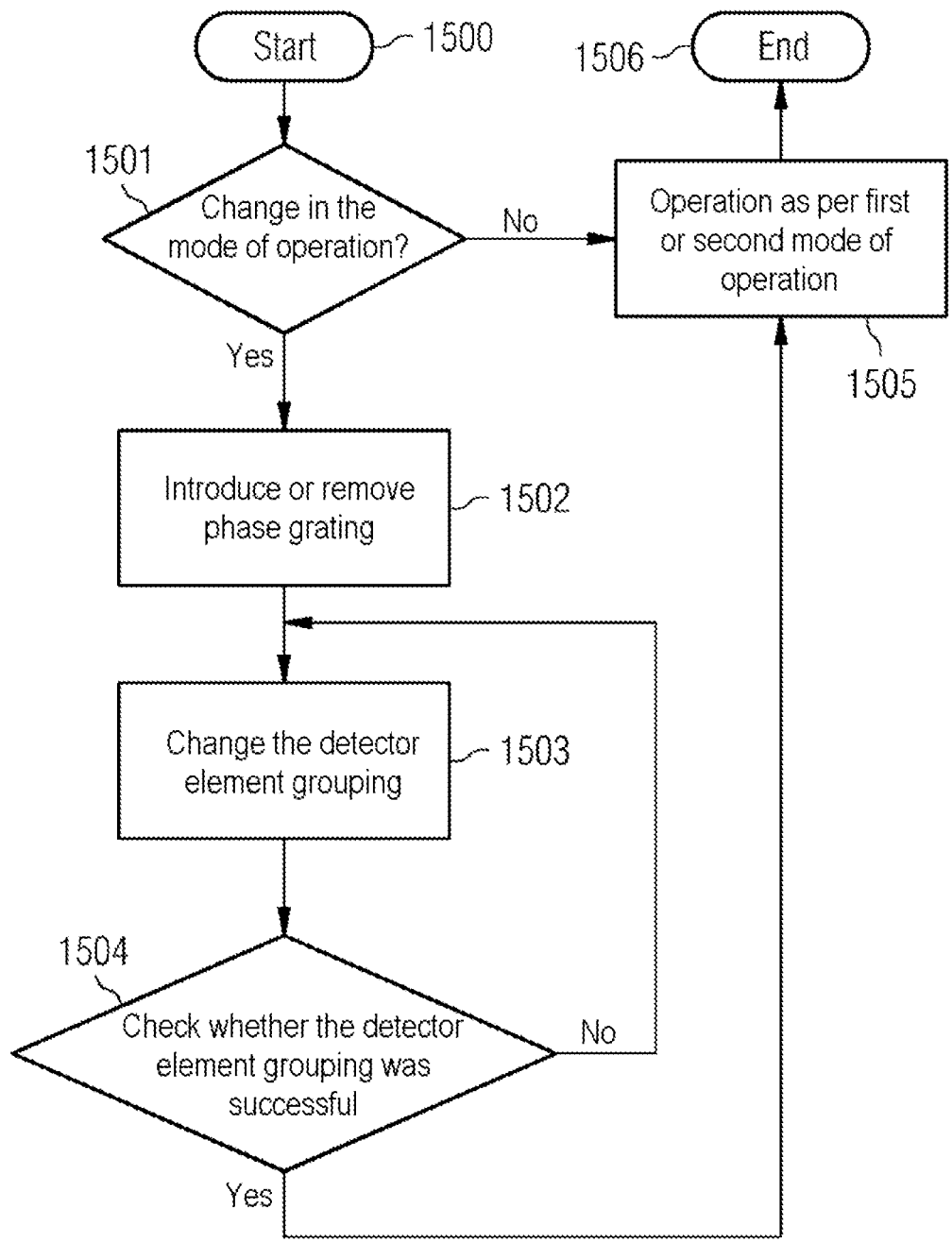

The above-described properties, features and advantages of this invention and the manner in which these are achieved will become clearer and easier to understand in conjunction with the following description of the exemplary embodiments, which are explained in more detail in conjunction with the drawings, wherein FIG. 1 is a view of an x-ray detector in accordance with the present invention, FIG. 2 is a schematic view of an x-ray detector in accordance with the present invention, wherein both a phase grating and an object to be examined are shown, FIG. 3 is a schematic view for illustrating the detector element groups for combining signal values in accordance with the present invention, FIG. 4 is a schematic view for illustrating the detector element groups for combining signal values in accordance with the present invention, FIG. 5 is a schematic view for illustrating the detector element groups for combining signal values in accordance with the present invention, wherein a phase jump locally modifies the x-ray beam phase value, FIG. 6 is a schematic view for illustrating the detector element groups for combining signal values in accordance with the present invention, wherein a phase jump locally modifies the x-ray beam phase value, FIG. 7 is a schematic sketch for calculating an x-ray beam phase value, FIG. 8 is a schematic sketch for calculating an x-ray beam phase value, FIG. 9 is a schematic view for illustrating the detector element groups for combining signal values in accordance with the present invention, FIG. 10 is a schematic view for illustrating the detector element groups for combining signal values in accordance with the present invention, wherein, in particular, neighboring detector elements do not have a fixed distance, FIG. 11 is a schematic flowchart of a method according to the invention, FIG. 12 is a schematic flowchart of a method in accordance with the present invention, with, in particular, setting the detector element evaluation distance and grouping of detector elements on the basis of the detector element evaluation distance being described in more detail, FIG. 13 is a schematic view of a grating-based phase contrast x-ray device, which comprises an x-ray detector in accordance with the present invention, FIG. 14 is a schematic view for illustrating the detector element groups for combining signal values in accordance with the present invention, in particular for illustrating a second mode of operation for operating the x-ray device for absorption x-ray imaging, and FIG. 15 is a schematic flowchart of a method in accordance with the present invention for switching between a first and a second mode of operation.

DESCRIPTION OF THE INVENTION

FIG. 1 shows an x-ray detector 1 according to the invention. Detector elements 3a, 3b, 3c are arranged two-dimensionally in a detector plane 7. Along the direction A, the detector elements 3a, 3b, 3c have a dimension 31, which is less than the dimension 32 along the direction B. The detector elements 3a, 3b, 3c are arranged as tightly as possible in the detector plane 7 in order to obtain a quanta yield which is as high as possible. In order to obtain good phase contrast spatial resolution with, at the same time, a large pixel area, the distance 30 between neighboring detector elements along the direction A is less than the distance between neighboring detector elements along the direction B. The detector elements 3a, 3b, 3c therefore have a rectangular cross section in the detector plane 7.

Using the parameter of the size of the detector elements along the directions A and B and the distance between neighboring detector elements along the directions A and B, it is possible to assign spatial resolutions along the directions A and B to the x-ray detector 1. The spatial resolution along the direction A is referred to as first spatial resolution while the spatial resolution along the direction B is referred to as second spatial resolution. The x-ray detector 1 as per FIG. 1 is able to resolve smaller features along the direction A than along the direction B. Therefore, the maximum possible spatial resolution along the direction A is higher than the maximum possible spatial resolution along the direction B.

X-ray detectors as per FIG. 1 of the present invention may be e.g. CCD or CMOS detectors. Such detector types contain substantially lithographic steps during the production, which steps define the dimensions of the individual detector elements 3a, 3b, 3c within the detector plane 7. In particular, semiconductor materials in standard production processes are also used during the production of CCD or CMOS sensors.

By way of example, typical dimensions 31, 32 of the detector elements 3a, 3b, 3c according to the present invention are: a dimension 31 of <10 μm, preferably <1 μm, along the direction A. Along the direction B: a dimension 32 of 80-100 μm. Such dimensions, firstly, permit a high spatial resolution and an accurate determination of an x-ray beam phase value, as will be explained in more detail below, and, secondly, such dimensions provide a sufficiently high sensitivity to x-ray beams.

FIG. 2 shows a schematic view of a grating-based phase contrast x-ray device as per the present invention. The x-ray detector 1 discussed in FIG. 1 is shown schematically for a row of detector elements 3a along the direction A. This is the direction of high spatial resolution in FIG. 1.

An x-ray beam source 20 generates x-ray beams. By way of example, the x-ray beam source 20 can generate x-ray beams, which have a frequency distribution and not a particularly long coherence length. By way of example, the energy of the x-ray beams can be 25 keV, but can, depending on application, also be up to e.g. 60 keV. In particular, the coherence length can lie in the sub-micrometer range. Arranged first in the beam path of the x-ray beams is a source grating 21. The source grating 21 is typically an absorption mask with a slit pattern arranged therein. After the x-ray beams have passed the source grating 21, they have at least partial coherence. Following this, an object 22 is arranged in the beam path of the x-ray beams. The object 22 can be the object to be examined. As indicated in FIG. 2 by arrows, the surface of the object 22 changes the orientation of the wavefronts of the x-ray beams. This can be associated with a change in the local phase of the wave shape of the x-ray beams.

A phase grating 23 is arranged following the object 22 in the beam path of the x-ray beams. Along the direction A, the phase grating 23 has a grating periodicity 23a. The grating periodicity 23a of the phase grating 23 along the direction A is typically in the range of a few micrometers, for example 4 µm or 10 µm.

The phase grating 23 generates an x-ray beam interference pattern 4 in the beam path of the x-ray beams. The Talbot effect forms the physical basis for this. The x-ray beam interference pattern 4 is characterized by minima 4b and maxima 4a of the local x-ray beam signal intensity, which minima 4b and maxima 4a are arranged periodically along the direction A and the position of which is characterized by an x-ray beam phase value. The x-ray beam interference pattern 4 has a periodicity 4c. The x-ray beam phase value at one point along the direction A in the x-ray beam interference pattern 4 downstream of the phase grating 23 is determined by the object 22. Accordingly, it is possible to draw conclusions about the object 22 by measuring the x-ray beam phase value. This is the object of the x-ray detector 1, which is arranged downstream of the phase grating 23 in the x-ray-beam beam path such that it can image the x-ray beam interference pattern 4.

The x-ray detector 1 consists of a multiplicity of detector elements 3a. In particular, the detector elements 3a have a first spatial resolution along the direction A, which renders it possible to locally resolve the position of the minima 4b and maxima 4a of the x-ray beam interference pattern 4 along the direction A and hence to determine the x-ray beam phase value. This enables the subsequent generation of an image of the x-ray beam phase value, which pictorially describes the object 22. Different phase values of the x-ray beams are present in different detector regions 2 of the x-ray detector 1. The detector regions 2 belonging to different phase values are delimited by phase jumps 5.

The phase jumps 5 are local changes in the phase of the x-ray beam interference pattern 4.

The characteristic dimensions of the detector regions 2 can be substantially greater than the dimensions of the individual detector elements 3 or the dimensions of the phase jumps. In other words: although a high first spatial resolution is required in the detector 1 in order to resolve the precise position of the minima 4b and maxima 4a of the x-ray beam interference pattern 4 and hence to determine the x-ray beam phase value, the x-ray beam phase value is to be assumed constant over relatively long distances. In particular, the characteristic length scale over which the x-ray beam phase value changes is determined by the object 22. Typically, the characteristic length of the changes in the x-ray beam phase value on the basis of the object 22 lies in the order of 100 µm or 200 µm, while the x-ray beam interference pattern 4 has a periodicity 4c, which lies in the region of a few micrometers.

The periodicity of the x-ray beam interference pattern 4c is decisively determined by the grating periodicity 23a of the phase grating 23. Further parameters, which flow into the determination of the exact periodicity 4c of the x-ray beam interference pattern 4 are, for example, the distance between the detector plane 7, in which the x-ray beam interference pattern 4 is observed, and the phase grating 23 or else the precise arrangement of the source grating 21. It is typically possible to calculate or predict with great accuracy the periodicity 4c of the x-ray beam interference pattern 4 when all decisive parameters of the grating-based phase contrast device are known.

The present invention employs the fact that the x-ray detector 1 provides a first spatial resolution along the direction A which, although it is suitable for precisely determining the x-ray beam phase value from the x-ray beam interference pattern 4, it is higher than would be necessary for resolving the decisive features of the object 22. This is explained in more detail on the basis of FIG. 3. FIG. 3 shows twelve detector elements 3a-3l of a detector 1 of the present invention. The detector elements 3a-3l are arranged within a detector region 2. The x-ray beam interference pattern 4 is imaged schematically. In FIG. 3, the detector region 2 does not contain any phase jumps 5.

In accordance with the present invention, the signal values of individual detector elements 3a-3l are combined to form group signal values. According to the invention, the combination can take place in a combination element. FIG. 3 and the following figures graphically indicate the combination of individual signal values to form group signal values. As is possible to gather from FIG. 3, the signal values of e.g. the detector elements 3a, 3d, 3g and 3j are combined in accordance with the present embodiment of the invention to form group signal value 6a. Furthermore, the signal values from detector elements 3b, 3e, 3h and 3k are combined to form group signal value 6b. Furthermore, the signal values from detector elements 3c, 3f, 3i and 3l are combined to form group signal value 6c. As can be gathered from FIG. 3, all detector elements 3a, 3d, 3g, 3j whose signal values are combined to form group signal value 6a, are arranged at positions along the direction A which are arranged at a location of maxima 4a of the x-ray beam interference pattern 4. By contrast, the detector elements 3b, 3c, 3e, 3f, 3h, 3i, 3k, 3l which are respectively combined to form group signal value 6b or 6c are arranged at locations along the direction A which lie in the vicinity of or at minima 4b of the x-ray beam interference pattern 4. In particular, the periodicity 4c of the x-ray beam interference pattern 4 is commensurable with the distance between neighboring detector elements 3a. 3d. 3g. 3j which are combined to form one group signal. Thus, the distance between neighboring detector elements, which are combined to form group signal value 6a, for example between detector elements 3a and 3d, is equal to twice the periodicity of the x-ray beam interference pattern 4.

By combining the signal values of every third detector element to form a group signal value, it is ensured that the respectively combined signal values correspond to the same phase of the x-ray beam interference pattern 4. The distance between two neighboring detector elements, which are combined to form the same group signal value, is defined as detector element evaluation distance 8a. Accordingly, the detector element evaluation distance 8a in FIG. 3 is double the size of the periodicity 4c of the x-ray beam interference pattern 4.

By contrast, FIG. 4 shows a situation in which the detector element evaluation distance 8b equals the periodicity 4c of the x-ray beam interference pattern 4. The distance 30 between neighboring detector elements is half the size in FIG. 4 as it is in FIG. 3. Accordingly, the first spatial resolution along the direction A is higher in FIG. 4 than in FIG. 3. FIG. 4 furthermore shows the subdivision of the detector elements 3a-3x into two detector regions 2a and 2b. Here, the detector regions 2 are not defined in relation to phase jumps 5 of the x-ray beam interference pattern 4, but rather in relation to the detector element groups in the various regions. Within the two detector regions 2a and 2b, three group signal values are in each case formed from combining the signal values of individual detector elements (from the detector elements 3a to 3e in the detector region 2a and from the detector elements 3m to 3x in the region 2b). In particular, the group signal values 6a, 6b and 6c are formed in the detector region 2a while the group signal values 6d, 6e and 6f are formed in the detector region 2b. In accordance with the present invention, an x-ray beam phase value can be calculated from the signal values 6a-6c, which phase value is characteristic for the detector region 2a. Accordingly, an x-ray beam phase value can be calculated from the group signal values 6d, 6e and 6f which is characteristic for the detector region 2b. If a spatially resolved image of the x-ray beam phase value is calculated in an image computing unit, the image resolution 9 of the image corresponds to the extent of the detector regions 2a and 2b. As can be seen from FIG. 4, the image resolution 9 of the image in particular is substantially lower than the distance 30 between neighboring detector elements along the direction A of the x-ray detector 1 or the first spatial resolution of the x-ray detector 1.

In particular, the image resolution 9 of the image of the embodiment shown in FIG. 4 is also twice the image resolution 9 of the image from FIG. 3. A result of this is depicted in FIGS. 5 and 6. Here, the detector 1 and the associated detector element groups from FIG. 5 correspond to the embodiment of FIG. 3. Moreover, the detector 1 and the associated detector element groups from FIG. 6 correspond to the embodiment of FIG. 4. However, the x-ray beam interference pattern 4 has a phase jump 5 in FIGS. 5 and 6. As can be identified immediately, the image resolution of the image 9 in FIG. 6 is sufficient to detect the change in the x-ray beam phase value due to the phase jump 5. The calculation of the x-ray beam phase values will supply a different value in the detector regions 2a and 2b in FIG. 6. However, the one large detector region 2 in FIG. 5 cannot provide an image resolution of the image 9 that would be high enough to resolve the change in the x-ray beam phase value as a result of the phase jump 5.

The comparison of FIGS. 3-6 makes it clear that the high first spatial resolution along the direction A of the detector 1 is only required for determining precisely the x-ray beam phase value within each detector range 2a or 2b. By contrast, decisive for an image resolution of the image 9 are the detector element groups or group signal values which are used for calculating the x-ray beam phase value. This calculation will be explained in more detail below on the basis of FIGS. 7 and 8.

FIGS. 7 and 8 schematically show how an x-ray beam phase value can be calculated from a plurality of group signal values 6a, 6b, 6c. In FIG. 7, three group signal values 6a, 6b and 6c are present. A position along the direction A can be assigned to the group signal values 6a, 6b, 6c. By way of example, this occurs from the knowledge of the position of the detector elements of a detector element group along the direction A. In this respect, reference is made to FIG. 2. The group signal values 6a-6c are measurement variables of the x-ray beam interference pattern 4 along the direction A. It is known that the x-ray beam interference pattern 4 is described by a trigonometric function, such as a sine or cosine function. Therefore, it is possible to use the group signal values 6a, 6b and 6c to determine the parameters such as amplitude and phase describing the trigonometric function.

The full line in FIG. 7 describes a trigonometric function in the form of a sine function, which describes the x-ray beam interference pattern 4 taking into account the measured group signal values 6a, 6b and 6c. In particular, the sine function is determined by a phase. This phase can be identified with the x-ray beam phase value. Therefore, in accordance with the preceding method, it is possible to determine the x-ray beam phase value from three group signal values.

It should be noted that it is also possible to use more than three group signal values for calculating the x-ray beam phase value. In general, the calculation of the x-ray beam phase value tends to be more accurate, the more group signal values are used for the calculation and the more accurately individual group signal values are known. In accordance with the present invention, four group signal values are preferably used to calculate the x-ray beam phase value, as explained on the basis of FIG. 7.

In FIG. 8, three group signal values 6a, 6b and 6c in turn describe an x-ray beam interference pattern 4. This x-ray beam interference pattern 4 is depicted using a dashed line, which represents a sine function. In particular, the x-ray beam interference pattern 4 is characterized by a phase jump 5 compared to the x-ray beam interference pattern 4 (full line) depicted in FIG. 7. Therefore, the group signal values 6a, 6b and 6c have different values compared to FIG. 7. In FIG. 8, it is also possible to calculate a phase value of the sine function on the basis of group signal values 6a, 6b and 6c and obtain the x-ray beam phase value therefrom.

FIG. 9 shows a further embodiment of the present invention in relation to combining signal values of different detector elements 3a-3n in different detector regions 2a and 2b of a detector 1. In accordance with the present invention, it may be advantageous to generate a first image resolution of the image 9a of the x-ray beam phase values in one detector region 2a of the detector 1. In the detector region 2a, the signal values of two detector elements are in each case combined to form the group signal values 6a-6f, for example from detector elements 3a and 3d for forming the group signal value 6a or from detector elements 3h and 3k for forming the group signal value 6e. Since in each case only two signal values of detector elements are combined to form a group signal value, the image resolution of the image 9a is high in the detector region 2a. In particular, the image resolution of the image 9a in the detector region 2a is higher than the image resolution of the image 9b in the detector region 2b. This is because, in the detector region 2b, three signal values of detector elements are combined to form a group signal value 6g-6l, for example the signal values of detector elements 3m, 3p and 3s are combined for forming the group signal value 6g.

In accordance with the present invention, it may be advantageous to use different number of signal values for forming a group signal value. The more signal values are combined to form a group signal value, the higher the group signal value and in particular the signal-to-noise ratio of the corresponding group signal value becomes. The measurement effectively becomes more sensitive. On the other hand, it is possible to reduce the x-ray beam dose in the case of an unchanging signal-to-noise ratio. However, the image resolution of the image 9 drops. Depending on the measurement object or objects to be examined, it may be advantageous to vary the number of combined signal values per group signal value, i.e. to vary the number of detector elements belonging to a detector element group.

In particular, in accordance with the present invention, it may be advantageous to combine a different number of signal values to form group signal values when measuring in different regions of the detector. By way of example, in edge regions of the measurement object 20, where there is already a high contrast due to the special type of measurement object, a high image resolution of the image 9 can be desirable. If the contrast is inherently provided due to the strong change in the object 22 in the edge region, it may be advantageous there to reduce the number of signal values that are combined to form a group signal value. FIGS. 2-6 show arrangements of detector elements 3, in which the detector elements are arranged along the direction A in a strictly periodic manner. However, in accordance with the present invention, it is not necessary for the detector elements 3 to be arranged strictly periodically along the direction A. FIG. 10 schematically depicts a case in which the strict periodicity of the detector elements along the direction A is not given. Detector elements 3a to 3z are arranged along the direction A, but the distance between neighboring detector elements varies as a function of the location along the direction A. In accordance with the present invention, the signal values from detector elements must continue to be combined in such a way that those signal values which correspond to a same phase of the x-ray beam interference pattern 4 are combined. It becomes clear from FIG. 5 that, for example, the signal values of detector elements 3a, 3d and 3n are combined. These detector elements have a position along the direction A, which coincides with the maxima 4a of the intensities of the x-ray beam interference pattern 4. In particular, the signal value of the detector element 3a corresponds to the first depicted maximum along the direction A, the position of the detector element 3d corresponds to the position of the second depicted maximum 4a along the direction A and the position of the detector element 3n corresponds to the position of the fifth depicted maximum 4a along the direction A. At the positions of the third and fourth depicted maxima 4a there are no detector elements which could be used for combination with the detector elements 3a, 3d and 3n to form a group signal value.

Furthermore, FIG. 10 shows that it is not necessary for all detector elements to be used to form a group signal value. In particular, the detector elements 3c, 3g, 3i, 3k, 3p, 3r, 3u, 3x and 3y are not used for the combination to form a group signal value. In terms of their position along the direction A, these detector elements deviate too much from the positions associated with the group signal values 6a-6d in respect of the x-ray beam interference pattern 4. Therefore, they cannot be used for combination with the group signal values 6a-6d.

In accordance with the present invention, it is therefore not mandatory for the various detector elements 3a-3z to have a fixed periodicity along the direction A. Rather, it is necessary for e.g. production-dependent variations in the periodicity of the detector elements along the direction A and the positions of the individual detector elements or their relative spacings to be known.

FIG. 11 shows a flowchart which schematically depicts a method in accordance with the present invention. The method in accordance with the present invention starts at step 1100. In accordance with one embodiment of the present invention, a detector region 2 can be set in step 1101. By way of example, as depicted in FIG. 4, a detector region 2 can be set in relation to different detector element groups along the direction A.

In step 1102, the signal values are captured. Capturing the signal values is accompanied by illuminating the object 22 using x-ray beams generated in an x-ray beam source 20. In particular, the object 22 is illuminated by x-ray beams for a measurement time duration. The measurement time duration and the amplitude of the x-ray beams used to illuminate the object 22 define an x-ray beam dose.

In step 1103, signal values are combined in the various detector regions. Signal values can be combined in a combination element in accordance with the present invention. Group signal values are calculated from the combined signal values. Combining the signal values can, in a preferred embodiment of the present invention, consist of a summation of various signal values. Further options for combining signal values to form group signal values would lie in e.g. multiplication, division or weighted addition.

In step 1104, an image of the x-ray beam phase value is calculated on the basis of the group signal values formed in step 1103. The calculation thereof can occur in an image computing unit in accordance with the present invention. In order to calculate an x-ray beam phase value, at least three, preferably at least four, different group signal values, which were combined in step 1103 from various signal values, are typically required. The x-ray beam phase value can be calculated as described in relation to FIG. 3.

As soon as the image of the x-ray beam phase value is calculated in step 1104, the method according to the present invention is terminated in step 1105. The image of the x-ray beam phase value is provided to a user.

As explained above, only a single exposure of the measurement object is required for creating the image of the x-ray beam phase value. In particular, there is no need for mechanical displacement of components during various measurement phases. This advantageously shortens the measurement time and enables a particularly efficient operation of an x-ray detector in accordance with the method under discussion.

FIG. 12 shows a further embodiment of a method in accordance with the present invention. In particular, FIG. 12 illustrates criteria for setting the detector element evaluation distance and criteria for selecting the detector elements which are combined to form a group signal value or criteria for forming detector element groups. The method as per FIG. 12 starts at step 1200. Initially, the detector element evaluation distance is set in a step 1201. The detector element evaluation distance is the distance between neighboring detector elements whose signal values are combined to form a group signal value.

A check is carried out in step 1202 as to whether the detector element evaluation distance, as set in step 1201, is commensurable to the signal periodicity. Here, commensurable means that the various detector elements whose signal values are combined to form a group signal value, are arranged along the direction A in such a way that the x-ray beam interference pattern 4 has the same phase at their positions. This is because if signal values of detector elements corresponding to different phases of the x-ray beam interference pattern are combined, the obtained group signal value is not representative for the signal value of the x-ray beam interference pattern at a specific phase. No image of the x-ray beam phase value can be calculated on the basis of such incorrect group signal values.

The check in step 1202 as to whether the detector element evaluation distance is in fact commensurable to the signal periodicity can be brought about in different ways. On the one hand, the signal periodicity can be calculated from the given parameters of the grating-based phase contrast x-ray device in accordance with the present invention. The calculated signal periodicity can be compared to the detector element evaluation distance when the distance of neighboring detector elements is known. Parameters which are necessary to calculate the signal periodicity of a grating-based phase contrast x-ray device according to the present invention are e.g.: type of x-ray beam source, type and periodicity of the source grating 21, type and periodicity of the phase grating 23, distance of the phase grating 23 from the detector plane 7.

However, furthermore, for example, if one or more of the aforementioned parameters are not known, it is also possible for a metrological test to be carried out within the scope of a reference measurement, which, in step 1202, shows in a metrological manner, whether the detector element evaluation distance is commensurable to the signal periodicity. Within the scope of a reference measurement, which preferably occurs without measurement object 22 in the beam path of the x-ray beams, there can be a test-type formation of group signal values. If the detector element evaluation distance is in fact commensurable to the signal periodicity, it is to be expected that respectively individual group signal values have minimal or maximal values. This is the case because, in the case of commensurability, the detector elements whose signal values are used to form the corresponding group signal values are arranged at positions of maximum or minimum intensity of the x-ray beam interference pattern 4.

By contrast, if the detector element evaluation distance is not commensurable to the signal periodicity, it is expected that various group signal values do not have very different values. This is the case because, if commensurability is lacking, the various detector elements whose signal values are combined to form a group signal value, cannot all be arranged precisely at one minimum 4b or maximum 4a of the x-ray beam interference pattern 4. In other words: in order to check the correct selection of the detector element evaluation distance in relation to the signal periodicity, there may be a maximization or minimization of individual group signal values within the scope of a reference measurement.

If it is determined in step 1202 that the detector element evaluation distance is commensurable to the signal periodicity, there can furthermore be the formation of groups on the basis of the previously determined detector element evaluation distance in step 1203. Forming groups typically contains the step of setting detector elements whose signal values are used to form an individual group signal value. By contrast, the number of group signal values, which are required for calculating an individual x-ray beam phase value (as, for example, explained with reference to FIG. 3), is already set by selecting the detector element evaluation distance and by the distance or the arrangement between neighboring detector elements in step 1202.

If detector elements were grouped in step 1203 to form the combination as group signal values, a check can be carried out in step 1204 as to whether, on the basis of this grouping, the spatial resolution of the image is too high. By way of example, it may be desirable that the spatial resolution of the image does not exceed a value which is associated with a specific number of pixels of the image of the x-ray beam phase value.

If the spatial resolution is identified as too high in step 1204, a further detector element 3 can be added to the respective combination in relation to a group signal value 6 in step 1207. By adding a further detector element 3 into a detector element group, the image resolution of the image 9 is simultaneously reduced. The check in step 1204 occurs until it is determined that the spatial resolution of the image is no longer too high.

Then there is the check in step 1205 as to whether the sensitivity of the measurement is too small. The sensitivity of the measurement is also decisively determined by the parameter of the number of detector elements whose signal values are combined to form a group signal value 6. If more signal values are combined to form a group signal value, the value of the corresponding group signal value increases. At the same time, the signal-to-noise ratio or the effective sensitivity increases. Thus, if it is determined in step 1205 that the sensitivity is too low, a detector element can be added in step 1207 to a group of the detector elements whose signal values are combined to form a group signal value. In step 1204, the check as to whether the spatial resolution is too high will subsequently result in the spatial resolution not being too high since it was previously reduced further. Accordingly, a check is once again carried out in step 1205 as to whether the sensitivity continues to be too small. The steps 1205 and 1207 are accordingly carried out until it is determined in step 1205 that the sensitivity of the measurement is sufficient due to a sufficiently high number of detector elements whose signal values are combined to form a group signal value.

In accordance with the check as per step 1205 as to whether the sensitivity is too low, there can be a check in step 1206 as to whether the x-ray beam dose is too high, for example in relation to a limit value. If it is determined in step 1206 that the x-ray beam dose is too high, a further detector element can be added to the group of detector elements whose signal values are combined to form a group signal value. In accordance with the description above in relation to step 1204 and 1205, this check occurs until it is successfully determined in step 1206 that the dose is not too high.

Subsequently, steps 1208, 1209 and 1210 are carried out, which correspond to the steps 1102, 1103 and 1104, which were explained above in relation to FIG. 11. The method as per the present invention subsequently terminates in step 1210.

FIG. 13 shows a schematic depiction of a grating-based phase contrast x-ray device as per the present invention. An x-ray beam source 20 and an object 22 are arranged in relation to a detector 1. The detector 1 comprises a phase grating 23. The parameters of the phase grating 23, such as both the precise arrangement in the detector and also the grating periodicity of the phase grating 23a, are known to an operating element 26 of the detector 1. The operating element 26 permits interaction with a user, and also the control of combination element 24, grouping member 25 and image computing unit 27. Combination element 24 combines the signal values of individual detector elements 3. The signal values from detector elements 3 of a detector element group are combined in accordance with the explanations made above and can be influenced by grouping member 25.

From the stipulation by operating element 26, grouping member 25 can determine the number of detector elements whose signal values are combined to form a group signal value or else set the detector evaluation distance in accordance with the stipulation of the grating periodicity 23a of the phase grating 23. The group signal values formed in combination element 24 are transmitted to image computing unit 27. Image computing unit 27 calculates an image of the x-ray beam phase value from the group signal values, as explained with reference to FIG. 3, and transmits this image to a unit not situated in the detector.

In particular, in accordance with the present invention, it is possible to provide a method which enables a user to bring about, for example by operating element 26, that the x-ray detector 1 generates an image which does not image the x-ray beam phase value as described above, but, for example, images an x-ray beam absorption value from conventional x-ray beam absorption imaging. To this end, it is necessary, for example, to remove the phase grating 23 from the region of the beam path of the x-ray beams upstream of the detector elements 3 and to modify the detector element group via grouping member 25. With respect to FIGS. 9 and 10, more detailed explanations are provided below in more detail as to how the switching between a first mode of operation, which enables generation of an image of the x-ray beam phase value in accordance with a grating-based phase contrast x-ray device of the present invention, and a second mode of operation, which enables the generation of an image of an x-ray beam absorption value in accordance with a conventional absorption x-ray device.

While the elements discussed with reference to FIG. 13, such as operating element 26, image computing unit 27, combination element 24 or grouping member 25 were discussed as separate units, it is nevertheless possible that, in one embodiment, individual ones of these units or the functions thereof are combined, for example in the form of a single unit. Individual components can still, for example, be implemented as hardware or software or as a combination thereof and can be embodied together or separately in one or more components.

FIG. 14 illustrates an option for grouping detector elements in order to form group signal values in the second mode of operation: in conventional absorption x-ray imaging, the x-ray signal to be detected has no periodicity along the direction A in the detector plane, unlike in phase contrast x-ray imaging. Therefore, it is not productive for absorption x-ray imaging to carry out a combination of signal values belonging to detector elements, as described on the basis of FIG. 2 for example.

By contrast, if an x-ray detector in accordance with the present invention is operated with a very small dimension of the detector elements along the direction A or with a very high spatial resolution, the sensitivity of the individual detector elements typically does not suffice for absorption x-ray imaging either. Therefore, it may also be necessary in the second mode of operation to combine signal values of detector elements along the direction A to form group signal values 6a-6c. As can be seen from FIG. 14, according to the present invention, this preferably happens in such a way that the signal values of neighboring detector elements, for example of the detector elements 3a and 3b, are used for the combination to form a group signal value. The number of detector elements whose signal values are combined to form group signal values 6a-6c, can assume different values, for example five in FIG. 14. By way of example, in FIG. 14, the signal values of detector elements 3a, 3b, 3c, 3d and 3e are combined to form group signal value 6a.

The number of detector elements 3 whose signal values are combined to form group signal values 6 decisively determines both the sensitivity of the absorption x-ray imaging and also the spatial resolution 9 of the image. By way of example, if more detector elements are grouped and the signal values thereof are combined to form group signal values, the spatial resolution 9 of the image sinks, but, at the same time, the effective sensitivity of the measurement rises since the value of the individual group signal values is higher. Naturally, the sensitivity of individual detector elements remains unchanged. In the case of an unchanging signal-to-noise ratio, this can lead to a reduction in the required x-ray beam signal dose. Depending on the measurement problem, it may accordingly be advantageous to vary the number of detector elements whose signal values are combined to form a group signal value.

With respect to FIG. 15, a method in accordance with the present invention is described, in which, in particular, it is possible to switch the mode of operation between a first mode of operation, corresponding to the grating-based phase contrast x-ray imaging, and a second mode of operation, the conventional absorption x-ray imaging. The method starts at step 1500. Initially, in step 1501, it is determined whether the user desires a change in the mode of operation. By way of example, such a change in mode of operation can be brought about by an operating element 26, as depicted in conjunction with FIG. 13. If the change in mode of operation is not desired, the operation can be continued in step 1505 in accordance with the first or the second mode of operation. The method ends in step 1506.

By contrast, if a change in mode of operation is desired, for example by the user, in step 1501, the phase grating is either introduced into the beam path of the x-ray beams or removed therefrom in step 1502. By way of example, if the change in mode of operation from the first to the second mode of operation is desired, i.e. if the transition from grating-based phase contrast x-ray imaging to conventional absorption x-ray imaging is desired, the phase grating 23 is removed from the beam path. Accordingly, the phase grating 23 is introduced into the beam path of the x-ray beams if a change is desired in step 1501 from the second to the first mode of operation.

Subsequently, the detector elements are regrouped in step 1503. Since the grouping of the detector elements in the first mode of operation and the second mode of operation differ greatly from one another (as depicted in relation to FIGS. 2 and 9), it is necessary in step 1503 to adapt the grouping of the detector elements for the subsequent combination of the signal values thereof to form group signal values. By way of example, the detector elements can be grouped by a grouping member 25 of the x-ray detector 1 as described in relation to FIG. 13.

While it may typically be advantageous in the first mode of operation if neighboring detector elements along the direction A do not belong to one group, i.e., if the signal values of neighboring detector elements are not combined to form a group signal value, it can, by contrast, be advantageous in the second mode of operation if the signal values of neighboring detector elements are combined to form one and the same group signal value. The various aspects of the grouping such as signal dose, signal sensitivity and spatial resolution of the image were explained in detail with reference to the earlier figures.

In step 1504, the check is carried out as to whether the detector element grouping was successful. By way of example, the check as per step 1504 can contain a check of the commensurability of the detector element evaluation distance as discussed in great detail with reference to FIG. 12, step 1202. Furthermore, the check as per step 1504 in relation to the second mode of operation (absorption x-ray imaging) can contain a check of the obtained image resolution 9 of the image of the absorption values of the x-ray beams. If the check of the detector element grouping in step 1504 is unsuccessful, there can be a regrouping in step 1503. This continues until the check in step 1504 is successful. Then, the method as per the currently discussed embodiment of the present invention can be continued in step 1505. The operation of the x-ray device in accordance with the present invention then occurs in accordance with the first or the second mode of operation. The method ends in step 1506.

Even though the invention was illustrated and described in more detail by the preferred exemplary embodiments, the invention is not restricted by the disclosed examples and other variations can be derived therefrom by a person skilled in the art, without departing from the scope of protection of the invention.

LIST OF REFERENCE SIGNS

1 Detector
2 Detector region
3 Detector element
4 X-ray beam interference pattern
4a Maximum of the x-ray beam interference pattern
4b Minimum of the x-ray beam interference pattern 4c Periodicity of the x-ray beam interference pattern
5 Phase jump
6 Group signal value
7 Detector plane
8 Detector element evaluation distance
9 Image resolution of the image
A Direction of the signal periodicity
B Direction perpendicular to the signal periodicity
20 X-ray beam source
21 Source grating
22 Object
23 Phase grating
23a Grating periodicity
24 Combination element
25 Grouping member
26 Operating element
27 Image computing unit
30 Detector element spacing along the direction A
31 Detector element dimension along the direction A
32 Detector element dimension along the direction B

The invention claimed is:

1. An x-ray detector of a grating-based phase contrast x-ray device, the x-ray detector comprising:
a plurality of detector elements for recording signal values of an x-ray signal, said plurality of detector elements being arranged in a two-dimensional array in a detector plane and providing, in the detector plane, a first spatial resolution in a first direction and a second spatial resolution in a second direction orthogonal to the first direction;
wherein said plurality of detector elements being disposed in at least two detector element groups, with at least two detector elements of said plurality of detector elements along the first direction belonging to each of said at least two detector element groups;
a combination element for combining signal values from said detector elements of one of said at least two detector element groups, to form a group signal value; and
an image computing unit for calculating a spatially resolved image of an x-ray beam phase value, said image computing unit calculating an x-ray beam phase value from, in each case, at least three group signal values, and said image computing unit being configured to calculate the spatially resolved image with an image resolution along the first direction that is lower than the first spatial resolution.

2. The x-ray detector according to claim 1, further comprising a phase grating disposed in a beam path of x-ray beams upstream of said detector plane and having a periodicity along the first direction.

3. The x-ray detector according to claim 2, wherein said combination element is configured to combine the signal values from detector elements of a detector element group of the at least two detector element groups, and wherein the signal values are grouped on a basis of at least a grating periodicity of the phase grating.

4. The x-ray detector according to claim 2, wherein said combination element is configured to combine the signal values from detector elements of a detector element group of the at least two detector element groups that have a spacing equal to one half the periodicity of the phase grating.

5. The x-ray detector according to claim 2, wherein the periodicity of said phase grating is greater by at least a factor of six than features resolved in accordance with the first spatial resolution.

6. The x-ray detector according to claim 1, wherein said image computing unit, to calculate the x-ray beam phase value, is configured to assign to the at least three group signal values a relative distance from one another and to calculate a trigonometric function described by the x-ray beam phase value, the trigonometric function describing the group signal value as a function of the relative distance and hence the x-ray beam phase value.

7. The x-ray detector according to claim 1, wherein said combination element is configured to combine the signal values from detector elements of a detector element group, in which a detector element evaluation distance, defined as distance between two mutually closest detector elements of the same detector element group along the first direction, is equal to an integer multiple of a local periodicity of the x-ray signal.

8. The x-ray detector according to claim 7, wherein the detector element evaluation distance is greater than the first spatial resolution.

9. The x-ray detector according to claim 7, wherein the distance between two neighboring detector elements along the first direction equals a quotient of integers of the local periodicity of the x-ray signal.

10. The x-ray detector according to claim 7, wherein the detector element evaluation distance equals a local periodicity of the x-ray signal.

11. The x-ray detector according to claim 1, wherein said combination element is configured to combine the signal values from detector elements such that neighboring detector elements belong to different detector element groups.

12. The x-ray detector according to claim 1, wherein said combination element is configured to sum the signal values from the detector elements.

13. The x-ray detector according to claim 1, wherein said combination element is configured to only combine the signal values from the detector elements arranged along the first direction.

14. The x-ray detector according to claim 1, wherein the first spatial resolution is higher than the second spatial resolution.

15. The x-ray detector according to claim 1, wherein the spatially resolved image of the x-ray beam phase value is an image calculated by said image computing unit from a single measurement.

16. The x-ray detector according to claim 1, wherein said plurality of detector elements are pixels of a CDD sensor or a CMOS sensor.

17. An x-ray detector of a grating-based phase contrast x-ray device, the x-ray detector comprising:
a plurality of detector elements for recording signal values of an x-ray signal, said plurality of detector elements being arranged in a two-dimensional array in a detector plane and providing, in the detector plane, a first spatial resolution in a first direction and a second spatial resolution in a second direction orthogonal to the first direction;
wherein said plurality of detector elements being disposed in at least two detector element groups, with at least two said detector elements of said plurality of detector elements along the first direction belonging to each of at least two said detector element groups;
a combination element for combining the signal values from said detector elements of one of said at least two detector element groups, to form a group signal value; and
an image computing unit for calculating a spatially resolved image of an x-ray beam phase value, said image computing unit calculating an x-ray beam phase value from, in each case, at least three group signal values;

the first spatial resolution being capable of resolving features down to 10 μm.

18. An x-ray detector of a grating-based phase contrast x-ray device, the x-ray detector comprising:
a plurality of detector elements for recording signal values of an x-ray signal, said plurality of detector elements being arranged in a two-dimensional array in a detector plane and providing, in the detector plane, a first spatial resolution in a first direction and a second spatial resolution in a second direction orthogonal to the first direction;
wherein said plurality of detector elements being disposed in at least two detector element groups, with at least two detector elements of said plurality of detector elements along the first direction belonging to each of at least two said detector element groups;
a combination element for combining the signal values from said detector elements of one of said at least two detector element groups, to form a group signal value;
an image computing unit for calculating a spatially resolved image of an x-ray beam phase value, said image computing unit calculating an x-ray beam phase value from, in each case, at least three group signal values; and
a grouping member configured to determine a number of detector elements belonging to a detector element group based on at least one criterion selected from the group of criteria consisting of an image resolution of the image, a signal intensity, and a time required to create the image.

19. A method of operating a grating-based phase contrast x-ray device and of evaluating signal values belonging to an x-ray signal from a plurality of detector elements of an x-ray detector that are arranged in a two- dimensional array in a detector plane, the method comprising the following steps:
capturing the signal values in the plurality of detector elements;
combining the signal values from at least two detector elements which, in each case, belong to one of at least two detector element groups to form detector element group signal values, wherein the at least two detector element groups are arranged along a spatial periodicity of the x-ray signal, which defines a first direction, in such a way that at least two detector elements belong to each detector element group of the at least two detector element groups, wherein a distance between closest detector elements of a detector element group defines a detector element evaluation distance, which is greater than a distance between neighboring detector elements in the first direction;
calculating an image of an x-ray beam phase value, wherein an x-ray beam phase value is calculated from at least three group signal values; and
setting the detector element evaluation distance on the basis of a local periodicity of the x-ray signal.

20. The method according to claim 19, further comprising, in order to calculate the x-ray beam phase value, assigning a relative distance from one another to the at least three group signal values and calculating a trigonometric function, described by the x-ray beam phase values; wherein the trigonometric function describes the group signal value as a function of the relative distance and hence the x-ray beam phase value.

21. The method according to claim 19, further comprising setting the detector elements to a group.

22. The method according to claim 19, wherein the detector element evaluation distance equals a local periodicity of the x-ray signal.

23. The method according to claim 19, wherein combining the signal values comprises summing the signal values.

24. The method according to claim 19, further comprising fixedly predetermining the detector element evaluation distance or an association of the detector elements with the respective detector element groups.

25. The method according to claim 19, further comprising setting a number of detector elements belonging to a group in accordance with at least one of the following criteria: an image resolution of the spatially resolved image, a signal intensity, a time until the spatially resolved image is calculated, a grating periodicity of a phase grating, which is arranged in the beam path of the x-ray beams upstream of the detector, and a distance of the phase grating of the x-ray detector plane.

26. A method of operating a grating-based phase contrast x-ray device and of evaluating signal values belonging to an x-ray signal from a plurality of detector elements of an x-ray detector that are arranged in a two-dimensional array in a detector plane, the method comprising the following steps:
capturing the signal values in the plurality of detector elements;
combining the signal values from at least two detector elements which, in each case, belong to one of at least two detector element groups to form detector element group signal values, wherein the detector element groups are arranged along a spatial periodicity of the x-ray signal, which defines a first direction, in such a way that at least two detector elements belong to each group of the at least two detector element groups, wherein a distance between closest detector elements of a detector element group defines a detector element evaluation distance, which is greater than a distance between neighboring detector elements in the first direction;
calculating an image of an x-ray beam phase value, wherein an x-ray beam phase value is calculated from at least three group signal values; and
setting the detector element evaluation distance based on a reference measurement.

27. The method according to claim 26, further comprising measuring the reference measurement by minimizing or maximizing group signal values as a function of the detector element evaluation distance.

28. A method of operating an x-ray device with an x-ray detector, the x-ray detector including a plurality of detector elements that are grouped and arranged two-dimensionally in a detector plane, the method comprising:
in a first mode of operation, operating the x-ray device as a grating-based phase contrast x-ray device in accordance with the method claim 19;
in a second mode of operation, operating the x-ray device as an absorption x-ray device.

29. The method according to claim 28, wherein the second mode of operation comprises the following steps:
capturing the signal values in the plurality of detector elements;
combining the signal values of grouped and mutually adjacent detector elements along a first direction in the detector plane to form group signal values; and
calculating a spatially resolved image of an x-ray beam absorption value, wherein calculating a spatially-resolved image of an x-ray beam absorption value comprises calculating an x-ray beam absorption value from, in each case, a group signal value.

30. The method according to claim 28, further comprising setting a number of combined signal values on the basis of one of the following criteria selected from the group consisting of: an image resolution of the spatially resolved image, an amplitude of the x-ray signal, and a time taken for creating the image.

31. The method according to claim 28, wherein the image resolution of the image is less than a spatial resolution of the x-ray detector in the first direction.

32. The method according to claim 28, further comprising a grouping step, for grouping the plurality of detector elements for subsequent combination in accordance with the first mode of operation or second mode of operation.

33. The method according to claim 32, wherein the grouping step for grouping the plurality of detector elements in accordance with the first mode of operation determines a local periodicity of the x-ray signal from at least one parameter selected from the group of parameters consisting of: a periodicity of a phase grating arranged in a beam path of the x-ray beams between an x-ray beam source and the detector plane, a distance of the phase grating from the detector plane, a maximization of a signal value in a reference measurement, and a minimization of a signal value in a reference measurement.

* * * * *